US010358420B2

(12) United States Patent
Minke et al.

(10) Patent No.: US 10,358,420 B2
(45) Date of Patent: *Jul. 23, 2019

(54) PROCESS FOR PREPARING AN N-METHYL-SUBSTITUTED TRIACETONAMINE COMPOUND

(71) Applicant: Evonik Degussa GmbH, Essen (DE)

(72) Inventors: Katharina Minke, Essen (DE); Benjamin Willy, Duesseldorf (DE); Felix Nissen, Nottuln (DE); Manfred Neumann, Marl (DE)

(73) Assignee: Evonik Degussa GmbH, Essen (DE)

(*) Notice: Subject to any disclaimer, the term of this patent is extended or adjusted under 35 U.S.C. 154(b) by 0 days.

This patent is subject to a terminal disclaimer.

(21) Appl. No.: 15/643,081

(22) Filed: Jul. 6, 2017

(65) Prior Publication Data
US 2018/0009752 A1 Jan. 11, 2018

(30) Foreign Application Priority Data
Jul. 7, 2016 (DE) .................. 10 2016 212 379

(51) Int. Cl.
C07C 67/08 (2006.01)
C07D 211/14 (2006.01)
C07D 401/14 (2006.01)
C07D 401/04 (2006.01)
C07D 401/12 (2006.01)
C07D 295/037 (2006.01)

(52) U.S. Cl.
CPC ........ C07D 211/14 (2013.01); C07D 295/037 (2013.01); C07D 401/04 (2013.01); C07D 401/12 (2013.01); C07D 401/14 (2013.01)

(58) Field of Classification Search
CPC .................................................. C07C 67/08
USPC ........................................................ 549/465
See application file for complete search history.

(56) References Cited

U.S. PATENT DOCUMENTS

| 4,110,331 | A | 8/1978 | Pettersson |
| 4,435,572 | A | 3/1984 | Rapoport et al. |
| 4,605,743 | A | 8/1986 | Malz, Jr. et al. |
| 5,130,429 | A | 7/1992 | Piccinelli et al. |
| 5,306,495 | A | 4/1994 | Cantatore et al. |
| 5,945,536 | A | 8/1999 | Jegelka et al. |
| 9,617,245 | B2 * | 4/2017 | Niemeyer ............ C07D 211/46 |
| 2008/0251758 | A1 | 10/2008 | Kirchhoff et al. |
| 2010/0074083 | A1 * | 3/2010 | Shibuya ............. C08K 5/34926 369/100 |
| 2016/0214937 | A1 | 7/2016 | Willy et al. |
| 2016/0214962 | A1 | 7/2016 | Niemeyer et al. |

FOREIGN PATENT DOCUMENTS

| CA | 2 060 546 C | 7/2002 |
| CN | 101768104 A | 7/2010 |
| CN | 105017131 A | 11/2015 |
| DE | 692 20 708 T2 | 1/1998 |
| EP | 0 047 967 A1 | 3/1982 |
| EP | 0 302 020 A2 | 2/1989 |
| EP | 0 302 020 A3 | 2/1989 |
| EP | 0 319 480 A2 | 6/1989 |
| EP | 0 319 480 A3 | 6/1989 |
| EP | 0 729 947 A1 | 9/1996 |
| EP | 0 857 719 A1 | 8/1998 |
| EP | 0 857 719 B1 | 4/2002 |
| EP | 3 048 097 A1 | 7/2016 |
| GB | 2 047 681 A | 12/1980 |
| JP | S53-105480 A | 9/1978 |
| JP | S62-56472 A | 3/1987 |
| JP | H02-133620 A | 5/1990 |
| JP | 2004-531611 A | 10/2004 |
| JP | 2008-214478 A | 9/2008 |
| JP | 2011-168566 A | 9/2011 |
| JP | 2014-105193 A | 6/2014 |
| WO | WO 2004/089913 A1 | 10/2004 |
| WO | WO 2005/123679 A2 | 12/2005 |
| WO | WO 2008/101979 A1 | 8/2008 |

OTHER PUBLICATIONS

Nishimura, Handbook of Heterogeneous Catalytic Hydrogenation for Organic Synthesis, Wiley, New York, 2001.*
Nerozzi, Platinum Metals Rev., 2012, 56, (4), 236-241.*
"Amine" Wikipedia, Aug. 8, 2016, pp. 1-9.
C. Harries, "Untersuchungen über die cyclischen Acetonbasen" European Journal of Organic Chemistry, vol. 417, XP002741350, 1918, pp. 107-191 with partial English translation.
J. Kirchhoff, et al., "Triacetoneamine Derivatives Industrial Applications and Recent Developments" RAPRA Technology Ltd., Addcon World '99, 1999, pp. 1-9 and cover page.
Ihor E. Kopka, et al., "Preparation of a Series of Highly Hindered Secondary Amines, Including Bis (Triethylcarbinyl) Amine" The Journal of Organic Chemistry, vol. 45, No. 23, 1980, pp. 4616-4622.
Wilson B. Lutz, et al., "New Derivatives of 2,2,6,6-Tetramethylpiperidine" The Journal of Organic Chemistry, vol. 27, May 1962, pp. 1695-1703.
Ana Minatti, et al., "Synthesis of Chiral 3-Substituted Indanones Via an Enantioselective Reductive-Heck Reaction" The Journal of Organic Chemistry, vol. 72, No. 24, 2007, pp. 9253-9258.
Jerzy Zakrzewski, et al., "Efficient Synthesis of 4-Isocyano-2,2,6,6-Tetramethylpiperidine-1-OXYL" Organic Preparations and Procedures International: The New Journal for Organic Synthesis, vol. 35, No. 4, XP 55197816, 2003, pp. 387-390 and cover page.
Anita H. Lewin, et al., "Molecular Features Associated with Polyamine Modulation of NMDA Receptors" Journal of Medicinal Chemistry, vol. 41, No. 6, 1998, pp. 988-995.
U.S. Appl. No. 15/643,540, filed Jul. 7, 2017, Katharina Minke, et al.
Extended European Search Report dated Sep. 15, 2017 in Patent Application No. 17178003.4 (with English translation of categories of cited documents).

(Continued)

Primary Examiner — Nizal S Chandrakumar
(74) Attorney, Agent, or Firm — Oblon, McClelland, Maier & Neustadt, L.L.P.

(57) ABSTRACT

An N-methyl-substituted triacetonamine compound can be produced by reacting at least one triacetonamine compound with formaldehyde under reductive conditions.

10 Claims, No Drawings

(56) References Cited

OTHER PUBLICATIONS

Extended Search report dated Dec. 12, 2017 in European Patent Application No. 17178013.3 (with English translation of category of cited documents).
Bojinov, "Novel polymerizable light emitting dyes—combination of a hindered amine with a 9-phenylxanthene fluorophore. Synthesis and photophysical investigations", Dyes and Pigments, vol. 74, 187-194, 2007.
Xia, et al. "Preparation of a Novel Stabilizer and its Thermal-Oxidative Stabilization Effect on Polyamide 6", Polymer Engineering and Science, 2197-2206, 2014.
"The fourth series of experimental chemistry 20, organic synthesis II—alcohol amine", p. 300 to 303, edited by The Chemical Society of Japan, issued on Apr. 25, 1996, Maruzen K.K.

* cited by examiner

PROCESS FOR PREPARING AN N-METHYL-SUBSTITUTED TRIACETONAMINE COMPOUND

BACKGROUND OF THE INVENTION

Field of the Invention

The present invention describes a process for preparing an N-methyl-substituted triacetonamine compound (triacetonamine="TAA"). The present invention particularly describes a process for methylating the nitrogen present in the ring, as shown, for example, in the reaction equation <1> (where R is, for example, an alkyl radical, an alkoxy radical, an amine radical or else an OH group):

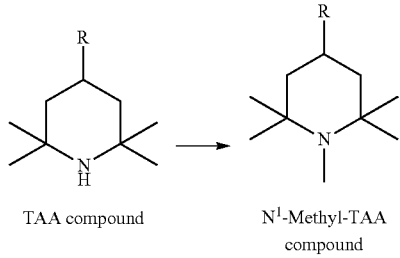

TAA compound → $N^1$-Methyl-TAA compound

Description of the Related Art

Methylated derivatives of 2,2,6,6-tetramethylpiperidine are employed with particular significance as "hindered amine light stabilizers" in particular. The methylation enables employment under acidic conditions as well. Commercial products having N-methylated 2,2,6,6-tetramethylpiperidine groups are, for example, Tinuvin® 292 [a mixture of 1-(methyl)-8-(1,2,2,6,6-pentamethyl-4-piperidinyl)sebacate and bis(1,2,2,6,6-pentamethyl-4-piperidinyl)sebacate] or Cyasorb® UV-3529 (CAS NUMBER 193098-40-7).

The prior art discloses various methods of methylating amines.

For example, Kopka, I. E., et al., *J. Org. Chem.* 1980, 45, 4616-4622 and Minatti, A., et al., *J. Org. Chem.* 2007, 72, 9253-9258 describe the reaction of amines with methyl halides. This is shown in schematic form in reaction equation <2> (where R is a radical as defined in relation to reaction equation <1>):

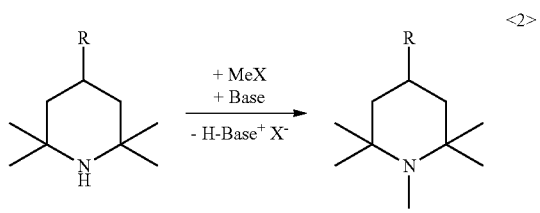

A disadvantage of the method shown in reaction equation <2> is that it is necessary to use at least one equivalent of a suitable base in addition to the methyl halide to release the product. This additionally leads to formation of the corresponding salts, which then arise as a waste product. An additional problem is that selective alkylation to give the tertiary amine is generally impossible since overalkylation to give the corresponding quaternary ammonium salt can take place.

A further method described in the prior art is the Eschweiler-Clarke reaction (e.g. Lutz, W. B., et al., *J. Org. Chem.* 1962, 27, 1695-1703; EP 0 729 947 A1; WO 2004/072035 A1; WO 2005/123679 A2). In this method, the amine is reacted with formaldehyde in the presence of formic acid. The formic acid functions as a reducing agent and is converted to $CO_2$. In order that the reaction proceeds, one equivalent of base is generally additionally required. The reaction is illustrated schematically in the following reaction equation <3> (where R is a radical as defined in relation to reaction equation <1>):

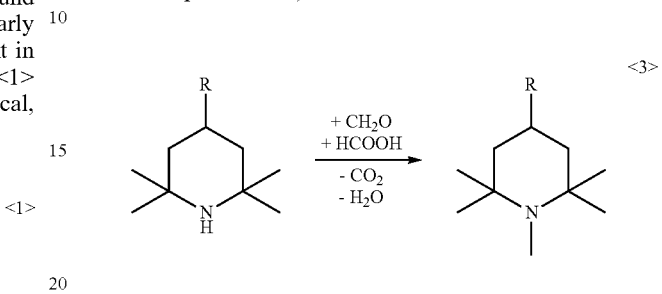

A disadvantage here is the need to use formic acid. Moreover, the use of the base again leads to generation of a corresponding waste stream.

A further means of N-methylation described in the prior art (e.g. WO 2004/089913 A1, WO 2008/101979 A1) is the reaction with formaldehyde in the presence of borohydrides (e.g. sodium borohydride). The reaction is illustrated schematically in the following reaction equation <4> (where R is a radical as defined in relation to reaction equation <1>):

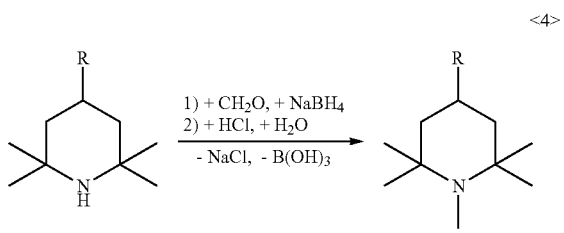

A disadvantage here is the need to use the borohydrides. The workup gives rise to large amounts of boric acid or boric acid derivatives as a waste stream.

SUMMARY OF THE INVENTION

The problem addressed by the present invention was therefore that of providing a process for preparing an N-methyl-substituted triacetonamine compound which does not have the aforementioned disadvantages.

A process which solves the problem described above has now surprisingly been found.

DETAILED DESCRIPTION OF THE INVENTION

The present invention relates, in a first aspect, to a process according to the following Points 1.1 to 1.11:

1.1 Process for preparing an N-methyl-substituted triacetonamine compound,
characterized in that at least one triacetonamine compound (I) is reacted with formaldehyde under reductive conditions,
where the triacetonamine compound (I) is selected from the group consisting of the chemical structures (I-A), (I-B), (I-C), (I-D), (I-E), (I-F), (I-G), (I-H) with

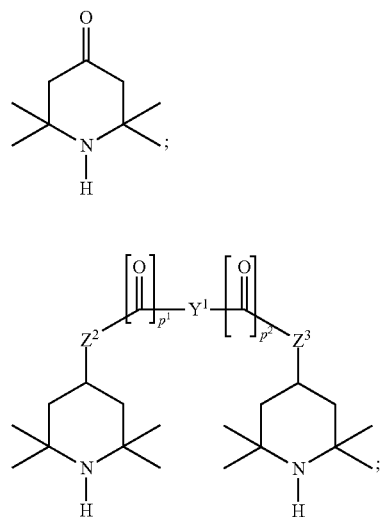
(I-A)
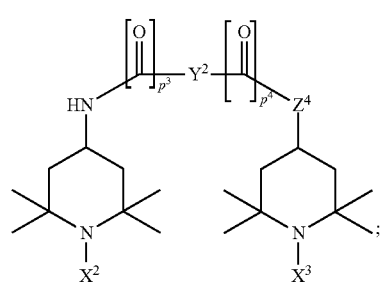
(I-C)
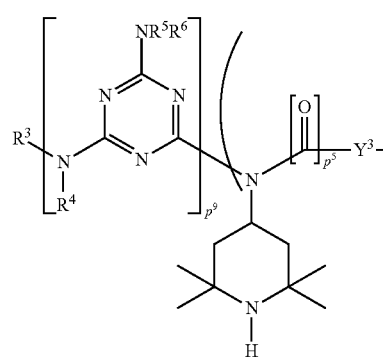
(I-E)
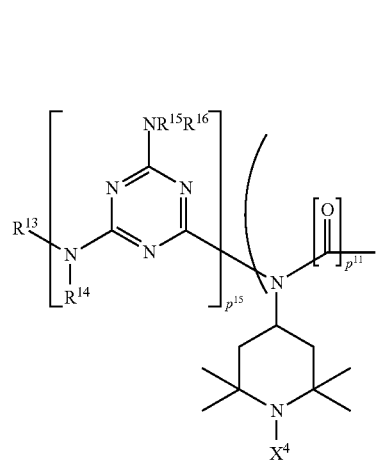
(I-F)
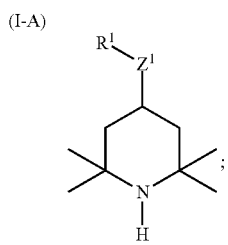
(I-B)
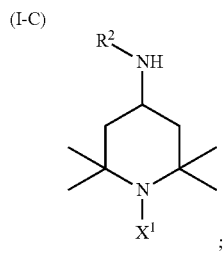
(I-D)
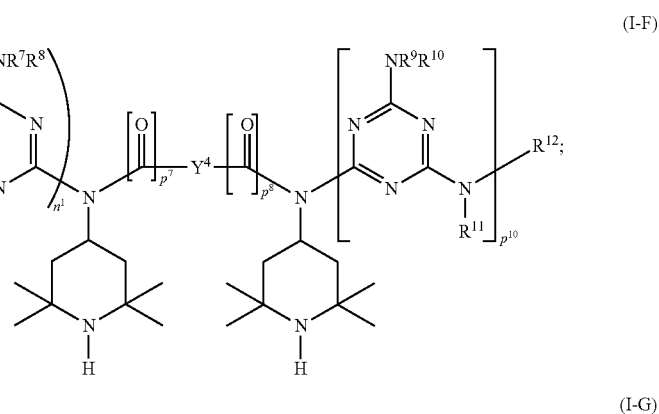
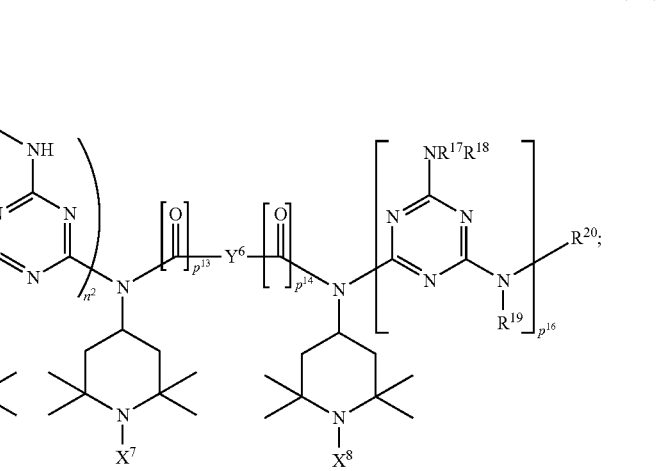
(I-G)

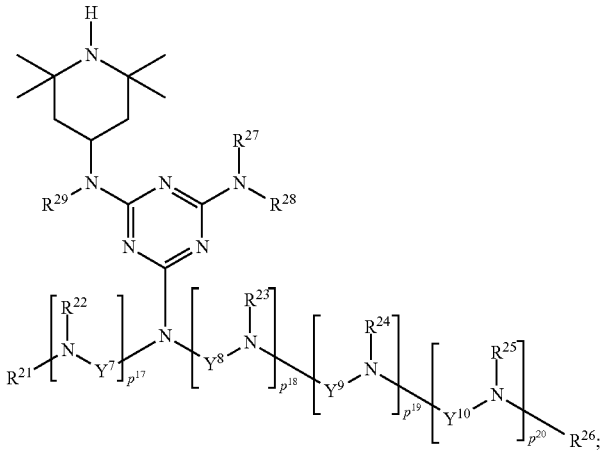

wherein $n^1$, $n^2$ are each independently an integer from the range of 1 to 20;

where $p^1$, $p^2$, $p^3$, $p^4$, $p^5$, $p^6$, $p^7$, $p^8$, $p^9$, $p^{10}$, $p^{11}$, $p^{12}$, $p^{13}$, $p^{14}$, $p^{15}$, $p^{16}$, $p^{17}$, $p^{18}$, $p^{19}$, $p^{20}$ are each independently 0 or 1;

where $X^1$ is selected from the group consisting of OH, —O., unbranched or branched alkyl group having 1 to 10 carbon atoms, unbranched or branched alkoxy group having 1 to 10 carbon atoms;

where $X^2$, $X^3$ are selected from the group consisting of hydrogen, OH, —O., unbranched or branched alkyl group having 1 to 10 carbon atoms, unbranched or branched alkoxy group having 1 to 10 carbon atoms, and where $X^2$, $X^3$ are each selected independently, with the exclusion of: $X^2=X^3$=hydrogen;

where $X^4$, $X^5$, $X^6$, $X^7$, $X^8$ are each independently selected from the group consisting of hydrogen, OH, —O, unbranched or branched alkyl group having 1 to 10 carbon atoms, unbranched or branched alkoxy group having 1 to 10 carbon atoms;

where $Y^1$, $Y^2$, $Y^3$, $Y^4$, $Y^5$, $Y^6$, $Y^7$, $Y^8$, $Y^9$, $Y^{10}$ are each independently selected from the group consisting of unbranched or branched alkylene group having 1 to 30 carbon atoms, divalent saturated hydrocarbyl group having 3 to 30 carbon atoms and having at least one saturated ring composed of 3 to 30 carbon atoms, divalent hydrocarbyl group having 6 to 30 carbon atoms, of which at least 6 carbon atoms are present in an aromatic system and the other carbon atoms, if present, are saturated, a bridging radical having a chemical structure selected from the group consisting of (i), (ii) with

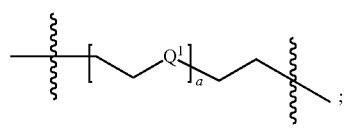

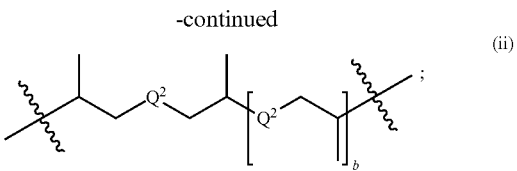

where $Q^1$, $Q^2$ are each independently selected from the group consisting of —O—, —S—, —NH— and —NR'— with R'=unbranched or branched alkyl group having 1 to 6 carbon atoms, where a is an integer selected from the range of 1 to 50,
where b is an integer selected from the range of 0 to 50,
and where $Y^1$ may also be a direct bond if at least one of $p^1$ and $p^2$ has the value of 1,
and where $Y^2$ may also be a direct bond if at least one of $p^3$ and $p^4$ has the value of 1,
and where $Y^3$ may also be a direct bond if at least one of $p^5$ and $p^6$ has the value of 1,
and where $Y^4$ may also be a direct bond if at least one of $p^7$ and $p^8$ has the value of 1,
and where $Y^5$ may also be a direct bond if at least one of $p^{11}$ and $p^{12}$ has the value of 1,
and where $Y^6$ may also be a direct bond if at least one of $p^{13}$ and $p^{14}$ has the value of 1;
and where $Z^1$, $Z^2$, $Z^3$, $Z^4$ are each independently selected from the group consisting of —O—, —S—, —NR$^{30}$—;
where the $R^1$, $R^2$, $R^3$, $R^4$, $R^5$, $R^6$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{30}$ radicals are each independently selected from the group consisting of hydrogen, unbranched or branched alkyl group which has 1 to 30 carbon atoms and in which at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$), unbranched or branched acyl group which has 1 to 30 carbon atoms and in which at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$);

a radical having a chemical structure selected from the group consisting of (iii), (iv), (v), (vi), (vii), (viii), (ix) with

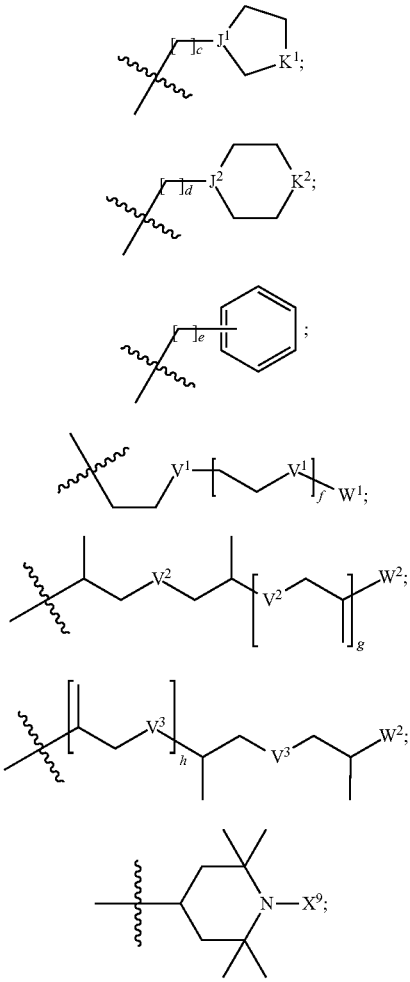

(iii)

(iv)

(v)

(vi)

(vii)

(viii)

(ix)

where $J^1$, $J^2$ are each independently selected from the group consisting of CH, N,
where $K^1$, $K^2$ are each independently selected from the group consisting of —O—, —NH—, —N(CH$_3$)—, —N(CH$_2$CH$_3$)—, —S—, —CH$_2$—,
where $V^1$, $V^2$, $V^3$ are each independently selected from the group consisting of —O—, —S—, —NH—, —NR"— with R"=unbranched or branched alkyl group having 1 to 6 carbon atoms,
where $W^1$, $W^2$, $W^3$ are each independently selected from the group consisting of H, methyl, ethyl,
where c, d, e, f, g, h are each independently an integer from the range of 0 to 50,
where $X^9$ is selected from the group consisting of hydrogen, —OH, —O, unbranched or branched alkyl group having 1 to 10 carbon atoms, unbranched or branched alkoxy group having 1 to 10 carbon atoms,
where, in the chemical structures (iii), (iv), (v), (vi), (vii), (viii), (ix), at least one hydrogen radical bonded to a carbon atom may be replaced by a radical selected from the group consisting of
—OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$);

where the $R^7$, $R^8$ radicals are each independently selected from the group consisting of
hydrogen,
unbranched or branched alkyl group which has 1 to 30 carbon atoms and in which at least one hydrogen radical may be replaced by a radical selected from the group consisting of
—OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$),
unbranched or branched acyl group which has 1 to 30 carbon atoms and in which at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$);
and where, when $p^9$=1, —NR$^3$R$^4$ may also be a radical of the chemical structure (x),
and where, when $p^{10}$=1, —NR$^{11}$R$^{12}$ may also be a radical of the chemical structure (x),
and where the —NR$^5$R$^6$, —NR$^7$R$^8$, —NR$^9$R$^{10}$ radicals may each independently also be a radical of the chemical structure (x),
where the chemical structure (x) is defined as follows:

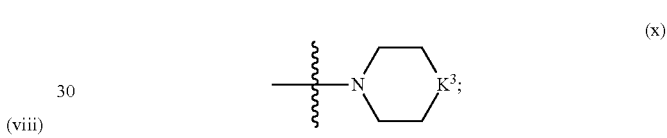

(x)

where $K^3$ is selected from the group consisting of —O—, —S—, —NH—, —N(CH$_3$)—, —N(CH$_2$CH$_3$)—, where $K^3$ is preferably —O—;
where the $R^{21}$, $R^{22}$, $R^{23}$, $R^{24}$, $R^{25}$, $R^{26}$ radicals are each independently selected from the group consisting of
hydrogen,
unbranched or branched alkyl group having 1 to 30 carbon atoms,
a group having the chemical structure (xi) with

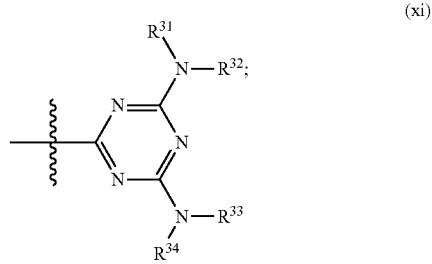

(xi)

where the $R^{27}$, $R^{28}$, $R^{29}$, $R^{31}$, $R^{32}$, $R^{33}$, $R^{34}$ radicals are each independently selected from the group consisting of
hydrogen,
unbranched or branched alkyl group which has 1 to 30 carbon atoms and in which at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$),
unbranched or branched acyl group which has 1 to 30 carbon atoms and in which at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$);

a radical having a chemical structure selected from the group consisting of (xii), (xiii), (xiv), (xv), (xvi), (xvii), (xviii) with

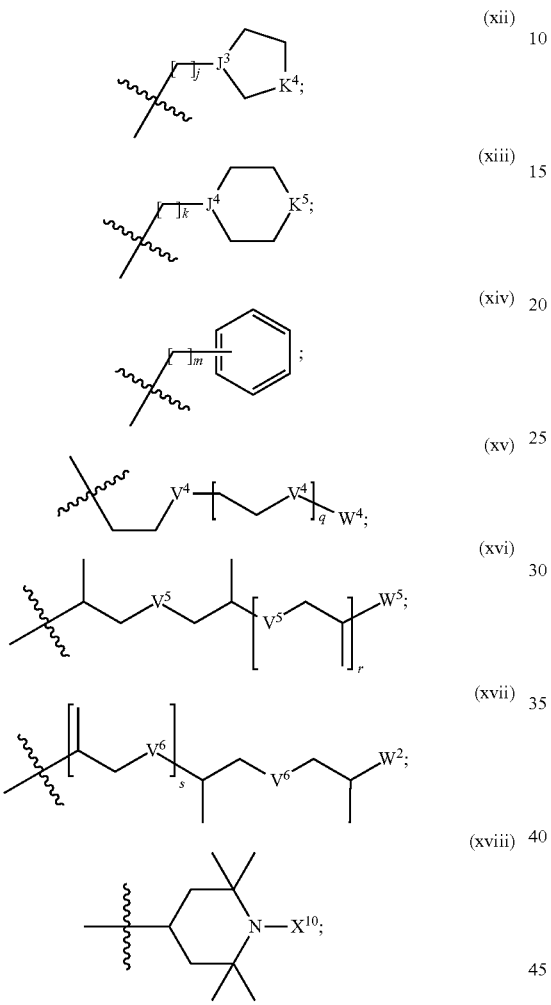

(xii)

(xiii)

(xiv)

(xv)

(xvi)

(xvii)

(xviii)

where J$^3$, J$^4$ are each independently selected from the group consisting of CH, N, where K$^4$, K$^5$ are each independently selected from the group consisting of —O—, —NH—, —N(CH$_3$)—, —N(CH$_2$CH$_3$)—, —S—, —CH$_2$—, where V$^4$, V$^5$, V$^6$ are each independently selected from the group consisting of —O—, —S—, —NH—, —NR'''— with R'''=unbranched or branched alkyl group having 1 to 6 carbon atoms, where W$^4$, W$^5$, W$^6$ are each independently selected from the group consisting of H, methyl, ethyl, where j, k, m, q, r, s are each independently an integer from the range of 0 to 50, where X$^{10}$ is selected from the group consisting of hydrogen, —OH, —O., unbranched or branched alkyl group having 1 to 10 carbon atoms, unbranched or branched alkoxy group having 1 to 10 carbon atoms, where, in the chemical structures (xii), (xiii), (xiv), (xv), (xvi), (xvii), (xviii), at least one hydrogen radical bonded to a carbon atom may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$), and with the proviso that R$^{21}$ and R$^{26}$, when $p^7=p^{18}=p^{19}=p^{20}=0$, may each independently also be a group of the chemical structure (xix) with

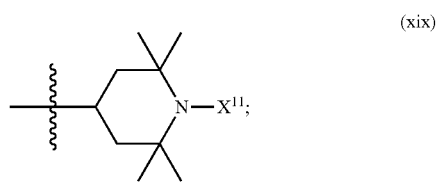

(xix)

where X$^{11}$ is selected from the group consisting of hydrogen, OH, —O., unbranched or branched alkyl group having 1 to 10 carbon atoms, unbranched or branched alkoxy group having 1 to 10 carbon atoms, and wherein reductive conditions are established by reacting the at least one triacetonamine compound (I) with formaldehyde in the presence of hydrogen and in the presence of an unsupported catalyst, where the unsupported catalyst includes at least one metal M, where the metal M is selected from the group consisting of Ag, V, Cr, Mo, Mn, Ni, Pd, Pt, Fe, Ru, Os, Co, Rh, Ir, Cu, especially Ag, Fe, Ni, Co, Cu, preferably Ni, Co, more preferably Ni.

1.2 Process according to Point 1.1, where $p^1=p^2=p^3=p^4=p^5=p^6=p^7=p^8=p^{11}=p^{12}=p^{13}=p^{14}=0$ and where $p^9, p^{10}, p^{15}, p^{16}, p^{17}, p^{18}, p^{19}, p^{20}$ are each independently 0 or 1.

1.3 Process according to Point 1.1 or 1.2, where Y$^1$, Y$^2$, Y$^3$, Y$^4$, Y$^5$, Y$^6$, Y$^7$, Y$^8$, Y$^9$, Y$^{10}$ are each independently selected from the group consisting of unbranched or branched alkylene group having 1 to 30 carbon atoms, divalent saturated hydrocarbyl group having 3 to 30 carbon atoms and having at least one saturated ring composed of 3 to 30 carbon atoms.

1.4 Process according to one or more of Points 1.1 to 1.3, where the R$^1$, R$^2$, R$^3$, R$^4$, R$^5$, R$^6$, R$^9$, R$^{10}$, R$^{11}$, R$^{12}$, R$^{13}$, R$^{14}$, R$^{15}$, R$^{16}$, R$^{17}$, R$^{18}$, R$^{19}$, R$^{20}$, R$^{30}$ radicals are each independently selected from the group consisting of hydrogen, unbranched or branched alkyl group which has 1 to 30 carbon atoms and in which at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$), a radical having a chemical structure (ix) with

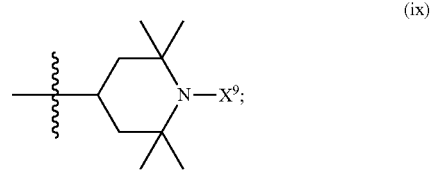

(ix)

where $X^9$ is selected from the group consisting of hydrogen, —OH, —O., unbranched or branched alkyl group having 1 to 10 carbon atoms, unbranched or branched alkoxy group having 1 to 10 carbon atoms;

where the $R^7$, $R^8$ radicals are each independently selected from the group consisting of hydrogen, unbranched or branched alkyl group which has 1 to 30 carbon atoms and in which at least one hydrogen radical may be replaced by a radical selected from the group consisting of —OH, —$NH_2$, —$OCH_3$, —$OCH_2CH_3$, —$NH(CH_3)$, —$N(CH_3)_2$, —$NH(CH_2CH_3)$, —$N(CH_2CH_3)_2$, —$N(CH_3)(CH_2CH_3)$, and where, when $p^9$=1, —$NR^3R^4$ may also be a radical of the chemical structure (x), and where, when $p^{10}$=1, —$NR^{11}R^{12}$ may also be a radical of the chemical structure (x), and where the —$NR^5R^6$, —$NR^7R^8$, —$NR^9R^{10}$ radicals may each independently also be a radical of the chemical structure (x), where the chemical structure (x) is defined as follows:

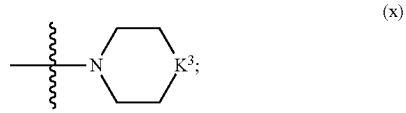

(x)

where $K^3$ is selected from the group consisting of —O—, —S—, —NH—, —N($CH_3$)—, —N($CH_2CH_3$)—, where $K^3$ is preferably —O—;

where the $R^{21}$, $R^{22}$, $R^{23}$, $R^{24}$, $R^{25}$, $R^{26}$ radicals are each independently selected from the group consisting of hydrogen, unbranched or branched alkyl group having 1 to 30 carbon atoms, a group having the chemical structure (xi) with

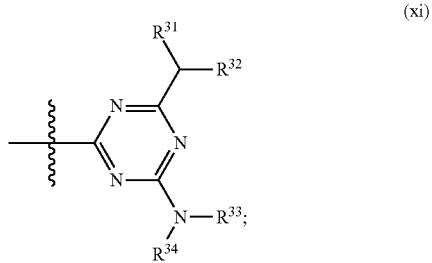

(xi)

where the $R^{27}$, $R^{28}$, $R^{29}$, $R^{31}$, $R^{32}$, $R^{33}$, $R^{34}$ radicals are each independently selected from the group consisting of hydrogen, unbranched or branched alkyl group which has 1 to 30 carbon atoms and in which at least one hydrogen radical may be replaced by a radical selected from the group consisting of —OH, —$NH_2$, —$OCH_3$, —$OCH_2CH_3$, —$NH(CH_3)$, —$N(CH_3)_2$, —$NH(CH_2CH_3)$, —$N(CH_2CH_3)_2$, —$N(CH_3)(CH_2CH_3)$, a radical having a chemical structure (xviii) with

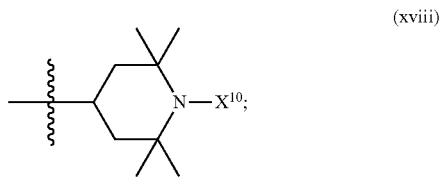

(xviii)

where $X^{10}$ is selected from the group consisting of hydrogen, —OH, —O., unbranched or branched alkyl group having 1 to 10 carbon atoms, unbranched or branched alkoxy group having 1 to 10 carbon atoms, and with the proviso that $R^{21}$ and $R^{26}$, when $p^{17}$=$p^{18}$=$p^{19}$=$p^{20}$=0, may each independently also be a group of the chemical structure (xix) with

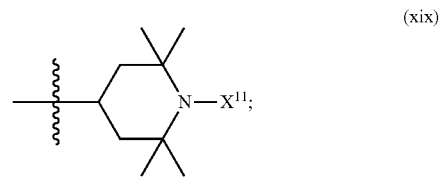

(xix)

where $X^{11}$ is selected from the group consisting of hydrogen, OH, —O., unbranched or branched alkyl group having 1 to 10 carbon atoms, unbranched or branched alkoxy group having 1 to 10 carbon atoms.

1.5 Process according to one or more of Points 1.1 to 1.4, where $X^4$=$X^5$=$X^6$=$X^7$=$X^8$=$X^9$=$X^{10}$=$X^{11}$=hydrogen.

1.6 Process according to one or more of Points 1.1 to 1.5, where the triacetonamine compound (I) is selected from the group consisting of the chemical structures (I-A), (I-B), (I-C), (I-D), (I-E).

1.7 Process according to one or more of Points 1.1 to 1.6, where the triacetonamine compound (I) is selected from the group consisting of the chemical structures (I-A), (I-B), (I-D), and where $Z^1$ is selected from the group consisting of —O—, —S—, —$NR^{30}$—;

where the $R^1$, $R^2$, $R^{30}$ radicals are each independently selected from the group consisting of hydrogen, unbranched or branched alkyl group which has 1 to 30 carbon atoms and in which at least one hydrogen radical may be replaced by a radical selected from the group consisting of —OH, —$NH_2$, —$OCH_3$, —$OCH_2CH_3$, —$NH(CH_3)$, —$N(CH_3)_2$, —$NH(CH_2CH_3)$, —$N(CH_2CH_3)_2$, —$N(CH_3)(CH_2CH_3)$.

1.8 Process according to one or more of Points 1.1 to 1.7, where the triacetonamine compound (I) is selected from the group consisting of the chemical structures (I-A), (I-B), (I-D)

and where $Z^1$ is selected from the group consisting of —O—, —$NR^{30}$—;

where the $R^1$, $R^2$, $R^{30}$ radicals are each independently selected from the group consisting of hydrogen, unbranched or branched alkyl group having 1 to 12 carbon atoms, preferably 1 to 6 carbon atoms.

1.9 Process according to one or more of Points 1.1 to 1.8, wherein formaldehyde is used as a gas, as an aqueous solution or as a solid, preferably as an aqueous solution or as a solid, more preferably as an aqueous solution.

1.10 Process according to one or more of Points 1.1 to 1.9, wherein the at least one triacetonamine compound (I) is reacted with formaldehyde under reductive conditions in at least one solvent, where the solvent is selected from the group consisting of aliphatic solvents, aromatic solvents, ethers, halogenated solvents, amides, thio compounds, carboxylic acids, alcohols, water.

1.11 Process according to one or more of Points 1.1 to 1.10, wherein the at least one triacetonamine compound (I) is reacted with formaldehyde under reductive conditions at a temperature in the range from 20° C. to 350° C. and a pressure in the range from 2 bar to 500 bar.

The present invention relates, in a second aspect, to a process according to the following Points 2.1 to 2.4:

2.1 Process for preparing an N-methyl-substituted triacetonamine compound, characterized in that a triacetonamine compound (I) is reacted with formaldehyde under reductive conditions, where the triacetonamine compound (I) has the chemical structure (I-A) with

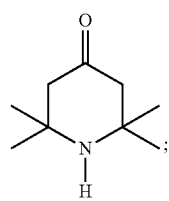

(I-A)

and wherein reductive conditions are established by reacting the at least one triacetonamine compound (I) with formaldehyde in the presence of hydrogen and in the presence of an unsupported catalyst, where the unsupported catalyst includes at least one metal M, where the metal M is selected from the group consisting of Ag, V, Cr, Mo, Mn, Ni, Pd, Pt, Fe, Ru, Os, Co, Rh, Ir, Cu, especially Ag, Fe, Ni, Co, Cu, preferably Ni, Co, more preferably Ni.

2.2 Process according to Point 2.1, wherein formaldehyde is used as a gas, as an aqueous solution or as a solid, preferably as an aqueous solution or as a solid, more preferably as an aqueous solution.

2.3 Process according to one or more of Points 2.1 to 2.2, wherein the triacetonamine compound (I) is reacted with formaldehyde under reductive conditions in at least one solvent, where the solvent is selected from the group consisting of aliphatic solvents, aromatic solvents, ethers, halogenated solvents, amides, thio compounds, carboxylic acids, alcohols, water.

2.4 Process according to one or more of Points 2.1 to 2.3, wherein the triacetonamine compound (I) is reacted with formaldehyde under reductive conditions at a temperature in the range from 20° C. to 350° C. and a pressure in the range from 2 bar to 500 bar.

The present invention relates, in a third aspect, to a process according to the following Points 3.1 to 3.8:

3.1 Process for preparing an N-methyl-substituted triacetonamine compound, characterized in that at least one triacetonamine compound (I) is reacted with formaldehyde under reductive conditions, where the triacetonamine compound (I) has the chemical structure (I-B) with

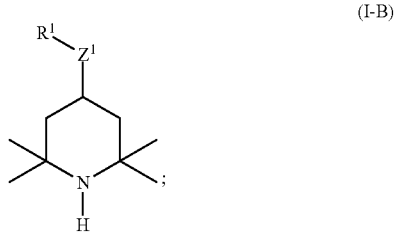

(I-B)

where $Z^1$ is selected from the group consisting of —O—, —S—, —NR$^{30}$—;

where the $R^1$, $R^{30}$ radicals are each independently selected from the group consisting of hydrogen, unbranched or branched alkyl group which has 1 to 30 carbon atoms and in which at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$), unbranched or branched acyl group which has 1 to 30 carbon atoms and in which at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$), a radical having a chemical structure selected from the group consisting of (iii), (iv), (v), (vi), (vii), (viii), (ix) with

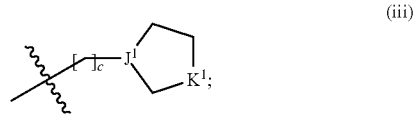

(iii)

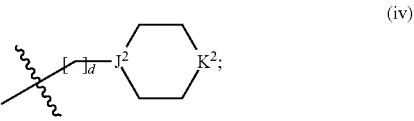

(iv)

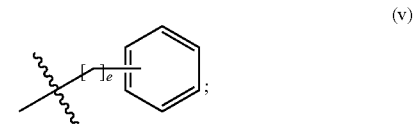

(v)

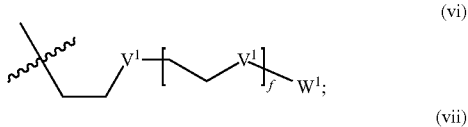

(vi)

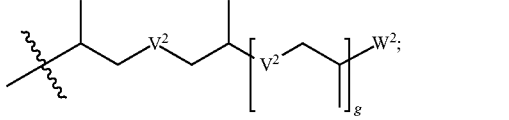

(vii)

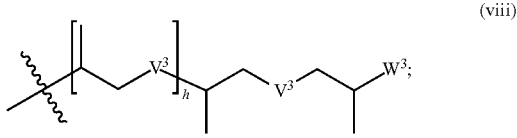

(viii)

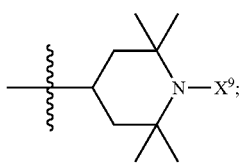

where J¹, J² are each independently selected from the group consisting of CH, N, where K¹, K² are each independently selected from the group consisting of —O—, —NH—, —N(CH₃)—, —N(CH₂CH₃)—, —S—, —CH₂—, where V¹, V², V³ are each independently selected from the group consisting of —O—, —S—, —NH—, —NR″— with R″=unbranched or branched alkyl group having 1 to 6 carbon atoms, where W¹, W², W³ are each independently selected from the group consisting of H, methyl, ethyl, where c, d, e, f, g, h are each independently an integer from the range of 0 to 50, where X⁹ is selected from the group consisting of hydrogen, —OH, —O., unbranched or branched alkyl group having 1 to 10 carbon atoms, unbranched or branched alkoxy group having 1 to 10 carbon atoms, where, in the chemical structures (iii), (iv), (v), (vi), (vii), (viii), (ix), at least one hydrogen radical bonded to a carbon atom may be replaced by a radical selected from the group consisting of
—OH, —NH₂, —OCH₃, —OCH₂CH₃, —NH(CH₃), —N(CH₃)₂, —NH(CH₂CH₃), —N(CH₂CH₃)₂, —N(CH₃)(CH₂CH₃), and wherein reductive conditions are established by reacting the at least one triacetonamine compound (I) with formaldehyde in the presence of hydrogen and in the presence of an unsupported catalyst, where the unsupported catalyst includes at least one metal M, where the metal M is selected from the group consisting of Ag, V, Cr, Mo, Mn, Ni, Pd, Pt, Fe, Ru, Os, Co, Rh, Ir, Cu, especially Ag, Fe, Ni, Co, Cu, preferably Ni, Co, more preferably Ni.

3.2 Process according to Point 3.1, where the R¹, R³⁰ radicals are each independently selected from the group consisting of
hydrogen,
unbranched or branched alkyl group which has 1 to 30 carbon atoms and in which at least one hydrogen radical may be replaced by a radical selected from the group consisting of —OH, —NH₂, —OCH₃, —OCH₂CH₃, —NH(CH₃), —N(CH₃)₂, —NH(CH₂CH₃), —N(CH₂CH₃)₂, —N(CH₃)(CH₂CH₃),
a radical having a chemical structure (ix) with

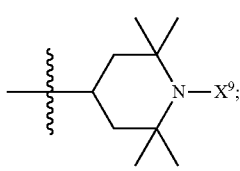

where X⁹ is selected from the group consisting of hydrogen, —OH, —O., unbranched or branched alkyl group having 1 to 10 carbon atoms, unbranched or branched alkoxy group having 1 to 10 carbon atoms.

3.3 Process according to Point 3.1 or 3.2, where X⁹=hydrogen.

3.4 Process according to one or more of Points 3.1 to 3.3, where the R¹, R³⁰ radicals are each independently selected from the group consisting of
hydrogen,
unbranched or branched alkyl group which has 1 to 30 carbon atoms and in which at least one hydrogen radical may be replaced by a radical selected from the group consisting of —OH, —NH₂, —OCH₃, —OCH₂CH₃, —NH(CH₃), —N(CH₃)₂, —NH(CH₂CH₃), —N(CH₂CH₃)₂, —N(CH₃)(CH₂CH₃).

3.5 Process according to one or more of Points 3.1 to 3.4, where
Z¹ is selected from the group consisting of —O—, —NR³⁰—;
where the R¹, R³⁰ radicals are each independently selected from the group consisting of
hydrogen,
unbranched or branched alkyl group having 1 to 12 and preferably 1 to 6 carbon atoms.

3.6 Process according to one or more of Points 3.1 to 3.5, wherein formaldehyde is used as a gas, as an aqueous solution or as a solid, preferably as an aqueous solution or as a solid, more preferably as an aqueous solution.

3.7 Process according to one or more of Points 3.1 to 3.6, wherein the at least one triacetonamine compound (I) is reacted with formaldehyde under reductive conditions in at least one solvent, where the solvent is selected from the group consisting of aliphatic solvents, aromatic solvents, ethers, halogenated solvents, amides, thio compounds, carboxylic acids, alcohols, water.

3.8 Process according to one or more of Points 3.1 to 3.7, wherein the at least one triacetonamine compound (I) is reacted with formaldehyde under reductive conditions at a temperature in the range from 20° C. to 350° C. and a pressure in the range from 2 bar to 500 bar.

The present invention relates, in a fourth aspect, to a process according to the following Points 4.1 to 4.10:

4.1 Process for preparing an N-methyl-substituted triacetonamine compound,
characterized in that at least one triacetonamine compound (I) is reacted with formaldehyde under reductive conditions,
where the triacetonamine compound (I) has the chemical structure (I-C) with

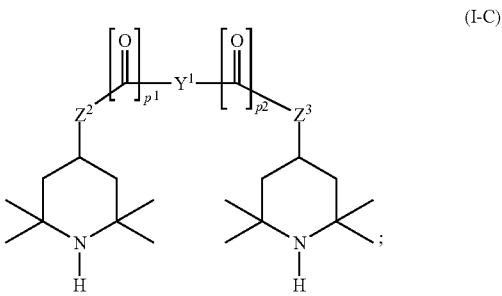

where p¹, p² are each independently 0 or 1;
where Y¹ is selected from the group consisting of
unbranched or branched alkylene group having 1 to 30 carbon atoms,
divalent saturated hydrocarbyl group having 3 to 30 carbon atoms and having at least one saturated ring composed of 3 to 30 carbon atoms, divalent hydrocarbyl group having 6 to 30 carbon atoms, of which at least 6 carbon atoms are present in an aromatic system and the other carbon atoms, if present, are saturated, a bridging radical having a chemical structure selected from the group consisting of (i), (ii) with

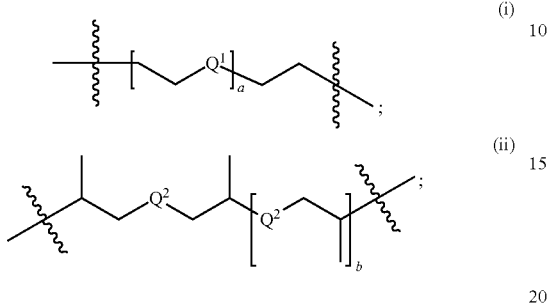

where
$Q^1$, $Q^2$ are each independently selected from the group consisting of —O—, —S—, —NH— and —NR'— with R'=unbranched or branched alkyl group having 1 to 6 carbon atoms,
where a is an integer selected from the range of 1 to 50,
where b is an integer selected from the range of 0 to 50,
and where $Y^1$ may also be a direct bond if at least one of $p^1$ and $p^2$ has the value of 1,
and where $Z^2$, $Z^3$ are each independently selected from the group consisting of —O—, —S—, —NR$^{30}$—;
where the $R^{30}$ radical is selected from the group consisting of
hydrogen,
unbranched or branched alkyl group which has 1 to 30 carbon atoms and in which at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$),
unbranched or branched acyl group which has 1 to 30 carbon atoms and in which at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$);
a radical having a chemical structure selected from the group consisting of (iii), (iv), (v), (vi), (vii), (viii), (ix) with

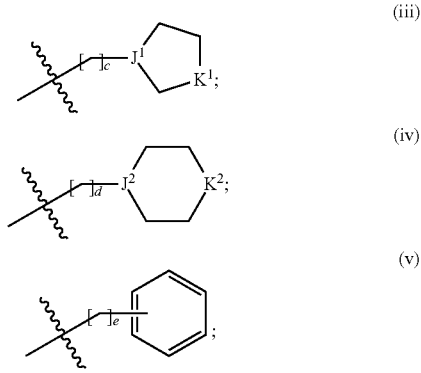

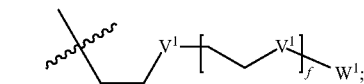

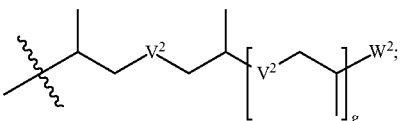

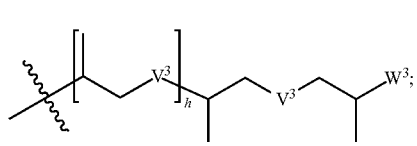

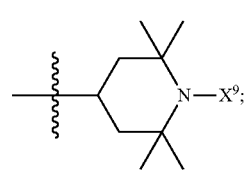

where $J^1$, $J^2$ are each independently selected from the group consisting of CH, N,
where $K^1$, $K^2$ are each independently selected from the group consisting of —O—, —NH—, —N(CH$_3$)—, —N(CH$_2$CH$_3$)—, —S—, —CH$_2$—,
where $V^1$, $V^2$, $V^3$ are each independently selected from the group consisting of —O—, —S—, —NH—, —NR"— with R"=unbranched or branched alkyl group having 1 to 6 carbon atoms,
where $W^1$, $W^2$, $W^3$ are each independently selected from the group consisting of H, methyl, ethyl,
where c, d, e, f, g, h are each independently an integer from the range of 0 to 50,
where $X^9$ is selected from the group consisting of hydrogen, —OH, —O., unbranched or branched alkyl group having 1 to 10 carbon atoms, unbranched or branched alkoxy group having 1 to 10 carbon atoms,
where, in the chemical structures (iii), (iv), (v), (vi), (vii), (viii), (ix), at least one hydrogen radical bonded to a carbon atom may be replaced by a radical selected from the group consisting of
—OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$),
and wherein reductive conditions are established by reacting the at least one triacetonamine compound (I) with formaldehyde in the presence of hydrogen and in the presence of an unsupported catalyst, where the unsupported catalyst includes at least one metal M, where the metal M is selected from the group consisting of Ag, V, Cr, Mo, Mn, Ni, Pd, Pt, Fe, Ru, Os, Co, Rh, Ir, Cu, especially Ag, Fe, Ni, Co, Cu, preferably Ni, Co, more preferably Ni.

4.2 Process according to Point 4.1, where $p^1$=$p^2$=0.

4.3 Process according to Point 4.1 or 4.2, where
$Y^1$ is selected from the group consisting of
unbranched or branched alkylene group having 1 to 30 carbon atoms,
divalent saturated hydrocarbyl group having 3 to 30 carbon atoms and having at least one saturated ring composed of 3 to 30 carbon atoms.

4.4 Process according to one or more of Points 4.1 to 4.3, where the R³⁰ radical is selected from the group consisting of hydrogen, unbranched or branched alkyl group which has 1 to 30 carbon atoms and in which at least one hydrogen radical may be replaced by a radical selected from the group consisting of —OH, —NH₂, —OCH₃, —OCH₂CH₃, —NH(CH₃), —N(CH₃)₂, —NH(CH₂CH₃), —N(CH₂CH₃)₂, —N(CH₃)(CH₂CH₃), a radical having a chemical structure (ix) with

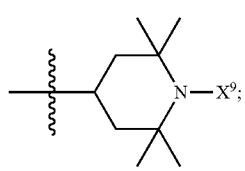

(ix)

where X⁹ is selected from the group consisting of hydrogen, —OH, —O., unbranched or branched alkyl group having 1 to 10 carbon atoms, unbranched or branched alkoxy group having 1 to 10 carbon atoms.

4.5 Process according to one or more of Points 4.1 to 4.4, where X⁹=hydrogen.

4.6 Process according to one or more of Points 4.1 to 4.5, where the R³⁰ radical is selected from the group consisting of hydrogen, unbranched or branched alkyl group which has 1 to 30 carbon atoms and in which at least one hydrogen radical may be replaced by a radical selected from the group consisting of —OH, —NH₂, —OCH₃, —OCH₂CH₃, —NH(CH₃), —N(CH₃)₂, —NH(CH₂CH₃), —N(CH₂CH₃)₂, —N(CH₃)(CH₂CH₃).

4.7 Process according to one or more of Points 4.1 to 4.6, where the R³⁰ radical is selected from the group consisting of hydrogen, unbranched or branched alkyl group having 1 to 12 and preferably 1 to 6 carbon atoms.

4.8 Process according to one or more of Points 4.1 to 4.7, wherein formaldehyde is used as a gas, as an aqueous solution or as a solid, preferably as an aqueous solution or as a solid, more preferably as an aqueous solution.

4.9 Process according to one or more of Points 4.1 to 4.8, wherein the at least one triacetonamine compound (I) is reacted with formaldehyde under reductive conditions in at least one solvent, where the solvent is selected from the group consisting of aliphatic solvents, aromatic solvents, ethers, halogenated solvents, amides, thio compounds, carboxylic acids, alcohols, water.

4.10 Process according to one or more of Points 4.1 to 4.9, wherein the at least one triacetonamine compound (I) is reacted with formaldehyde under reductive conditions at a temperature in the range from 20° C. to 350° C. and a pressure in the range from 2 bar to 500 bar.

The present invention relates, in a fifth aspect, to a process according to the following Points 5.1 to 5.8:

5.1 Process for preparing an N-methyl-substituted triacetonamine compound, characterized in that at least one triacetonamine compound (I) is reacted with formaldehyde under reductive conditions, where the triacetonamine compound (I) has the chemical structures (I-D) with

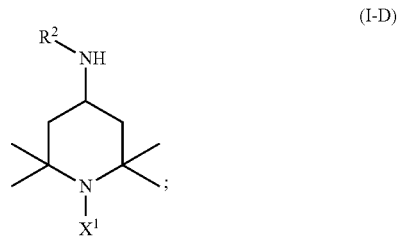

(I-D)

where X¹ is selected from the group consisting of OH, —O., unbranched or branched alkyl group having 1 to 10 carbon atoms, unbranched or branched alkoxy group having 1 to 10 carbon atoms;

where the R² radical is selected from the group consisting of hydrogen, unbranched or branched alkyl group which has 1 to 30 carbon atoms and in which at least one hydrogen radical may be replaced by a radical selected from the group consisting of —OH, —NH₂, —OCH₃, —OCH₂CH₃, —NH(CH₃), —N(CH₃)₂, —NH(CH₂CH₃), —N(CH₂CH₃)₂, —N(CH₃)(CH₂CH₃), unbranched or branched acyl group which has 1 to 30 carbon atoms and in which at least one hydrogen radical may be replaced by a radical selected from the group consisting of —OH, —NH₂, —OCH₃, —OCH₂CH₃, —NH(CH₃), —N(CH₃)₂, —NH(CH₂CH₃), —N(CH₂CH₃)₂, —N(CH₃)(CH₂CH₃), a radical having a chemical structure selected from the group consisting of (iii), (iv), (v), (vi), (vii), (viii), (ix) with

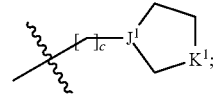

(iii)

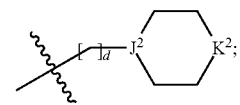

(iv)

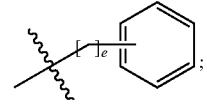

(v)

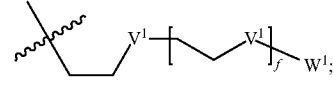

(vi)

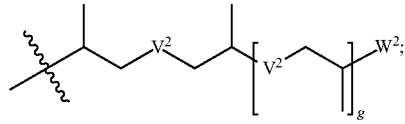

(vii)

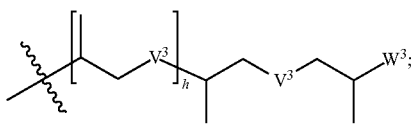

(viii)

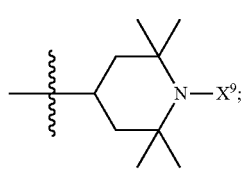

(ix)

where J$^1$, J$^2$ are each independently selected from the group consisting of CH, N,
where K$^1$, K$^2$ are each independently selected from the group consisting of —O—, —NH—, —N(CH$_3$)—, —N(CH$_2$CH$_3$)—, —S—, —CH$_2$—,
where V$^1$, V$^2$, V$^3$ are each independently selected from the group consisting of —O—, —S—, —NH—, —NR"— with R"=unbranched or branched alkyl group having 1 to 6 carbon atoms,
where W$^1$, W$^2$, W$^3$ are each independently selected from the group consisting of H, methyl, ethyl,
where c, d, e, f, g, h are each independently an integer from the range of 0 to 50,
where X$^9$ is selected from the group consisting of hydrogen, —OH, —O., unbranched or branched alkyl group having 1 to 10 carbon atoms, unbranched or branched alkoxy group having 1 to 10 carbon atoms,
where, in the chemical structures (iii), (iv), (v), (vi), (vii), (viii), (ix), at least one hydrogen radical bonded to a carbon atom may be replaced by a radical selected from the group consisting of
—OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$),
and wherein reductive conditions are established by reacting the at least one triacetonamine compound (I) with formaldehyde in the presence of hydrogen and in the presence of an unsupported catalyst, where the unsupported catalyst includes at least one metal M, where the metal M is selected from the group consisting of Ag, V, Cr, Mo, Mn, Ni, Pd, Pt, Fe, Ru, Os, Co, Rh, Ir, Cu, especially Ag, Fe, Ni, Co, Cu, preferably Ni, Co, more preferably Ni.

5.2 Process according to Point 5.1, where the R$^2$ radical is selected from the group consisting of
hydrogen,
unbranched or branched alkyl group which has 1 to 30 carbon atoms and in which at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$),
a radical having a chemical structure (ix) with

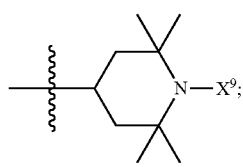

(ix)

where X$^9$ is selected from the group consisting of hydrogen, —OH, —O., unbranched or branched alkyl group having 1 to 10 carbon atoms, unbranched or branched alkoxy group having 1 to 10 carbon atoms.

5.3 Process according to Point 5.1 or 5.2, where X$^9$=hydrogen.

5.4 Process according to one or more of Points 5.1 to 5.3, where the R$^2$ radical is selected from the group consisting of
hydrogen,
unbranched or branched alkyl group which has 1 to 30 carbon atoms and in which at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$).

5.5 Process according to one or more of Points 5.1 to 5.4, where the R$^2$ radical is selected from the group consisting of
hydrogen,
unbranched or branched alkyl group having 1 to 12 and preferably 1 to 6 carbon atoms.

5.6 Process according to one or more of Points 5.1 to 5.5, wherein formaldehyde is used as a gas, as an aqueous solution or as a solid, preferably as an aqueous solution or as a solid, more preferably as an aqueous solution.

5.7 Process according to one or more of Points 5.1 to 5.6, wherein the at least one triacetonamine compound (I) is reacted with formaldehyde under reductive conditions in at least one solvent, where the solvent is selected from the group consisting of aliphatic solvents, aromatic solvents, ethers, halogenated solvents, amides, thio compounds, carboxylic acids, alcohols, water.

5.8 Process according to one or more of Points 5.1 to 5.7, wherein the at least one triacetonamine compound (I) is reacted with formaldehyde under reductive conditions at a temperature in the range from 20° C. to 350° C. and a pressure in the range from 2 bar to 500 bar.

The present invention relates, in a sixth aspect, to a process according to the following Points 6.1 to 6.10:

6.1 Process for preparing an N-methyl-substituted triacetonamine compound,
characterized in that at least one triacetonamine compound (I) is reacted with formaldehyde under reductive conditions,
where the triacetonamine compound (I) has the chemical structures (I-E) with

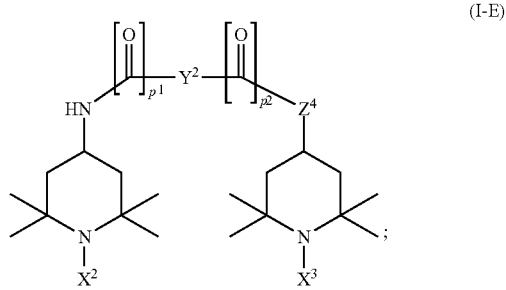

(I-E)

where p$^3$, p$^4$ are each independently 0 or 1;
where X$^2$, X$^3$ are selected from the group consisting of hydrogen, OH, —O., unbranched or branched alkyl group having 1 to 10 carbon atoms, unbranched or branched alkoxy group having 1 to 10 carbon atoms, and where X$^2$, X$^3$ are each selected independently, with the exclusion of: X$^2$=X$^3$=hydrogen;

where $Y^2$ is selected from the group consisting of
unbranched or branched alkylene group having 1 to 30 carbon atoms,
divalent saturated hydrocarbyl group having 3 to 30 carbon atoms and having at least one saturated ring composed of 3 to 30 carbon atoms,
divalent hydrocarbyl group having 6 to 30 carbon atoms, of which at least 6 carbon atoms are present in an aromatic system and the other carbon atoms, if present, are saturated,
a bridging radical having a chemical structure selected from the group consisting of (i), (ii) with

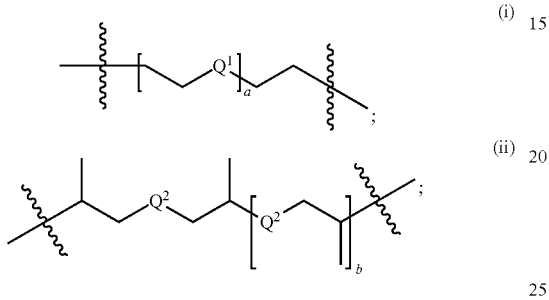

where
$Q^1$, $Q^2$ are each independently selected from the group consisting of —O—, —S—, —NH— and —NR'— with R'=unbranched or branched alkyl group having 1 to 6 carbon atoms,
where a is an integer selected from the range of 1 to 50,
where b is an integer selected from the range of 0 to 50,
and where $Y^2$ may also be a direct bond if at least one of $p^3$ and $p^4$ has the value of 1,
and where $Z^4$ is selected from the group consisting of —O—, —S—, —NR$^{30}$—;
where the $R^{30}$ radical is selected from the group consisting of
hydrogen,
unbranched or branched alkyl group which has 1 to 30 carbon atoms and in which at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$),
unbranched or branched acyl group which has 1 to 30 carbon atoms and in which at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$);
a radical having a chemical structure selected from the group consisting of (iii), (iv), (v), (vi), (vii), (viii), (ix) with

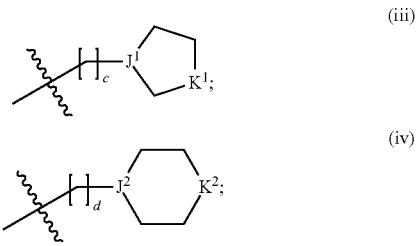

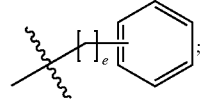

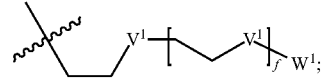

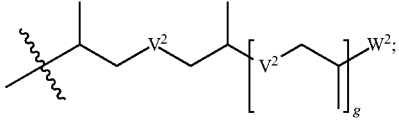

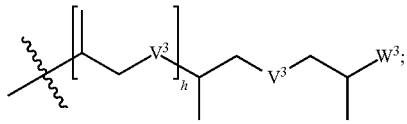

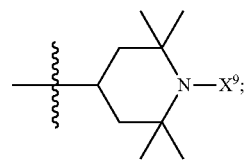

where $J^1$, $J^2$ are each independently selected from the group consisting of CH, N,
where $K^1$, $K^2$ are each independently selected from the group consisting of —O—, —NH—, —N(CH$_3$)—, —N(CH$_2$CH$_3$)—, —S—, —CH$_2$—,
where $V^1$, $V^2$, $V^3$ are each independently selected from the group consisting of —O—, —S—, —NH—, —NR"— with R"=unbranched or branched alkyl group having 1 to 6 carbon atoms,
where $W^1$, $W^2$, $W^3$ are each independently selected from the group consisting of H, methyl, ethyl,
where c, d, e, f, g, h are each independently an integer from the range of 0 to 50,
where $X^9$ is selected from the group consisting of hydrogen, —OH, —O., unbranched or branched alkyl group having 1 to 10 carbon atoms, unbranched or branched alkoxy group having 1 to 10 carbon atoms,
where, in the chemical structures (iii), (iv), (v), (vi), (vii), (viii), (ix), at least one hydrogen radical bonded to a carbon atom may be replaced by a radical selected from the group consisting of
—OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$),
and wherein reductive conditions are established by reacting the at least one triacetonamine compound (I) with formaldehyde in the presence of hydrogen and in the presence of an unsupported catalyst, where the unsupported catalyst includes at least one metal M, where the metal M is selected from the group consisting of Ag, V, Cr, Mo, Mn, Ni, Pd, Pt, Fe, Ru, Os, Co, Rh, Ir, Cu, especially Ag, Fe, Ni, Co, Cu, preferably Ni, Co, more preferably Ni.
6.2 Process according to Point 6.1, where $p^3=p^4=0$.
6.3 Process according to Point 6.1 or 6.2, where
$Y^2$ is selected from the group consisting of
unbranched or branched alkylene group having 1 to 30 carbon atoms, divalent saturated hydrocarbyl group having 3 to 30 carbon atoms and having at least one saturated ring composed of 3 to 30 carbon atoms.

6.4 Process according to one or more of Points 6.1 to 6.3, where the $R^{30}$ radical is selected from the group consisting of
hydrogen,
unbranched or branched alkyl group which has 1 to 30 carbon atoms and in which at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$),
a radical having a chemical structure (ix) with

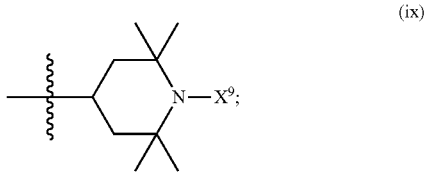

(ix)

where $X^9$ is selected from the group consisting of hydrogen, —OH, —O., unbranched or branched alkyl group having 1 to 10 carbon atoms, unbranched or branched alkoxy group having 1 to 10 carbon atoms.

6.5 Process according to one or more of Points 6.1 to 6.4, where the $R^{30}$ radical is selected from the group consisting of
hydrogen,
unbranched or branched alkyl group having 1 to 12 carbon atoms, 6.6 Process according to one or more of Points 6.1 to 6.5, where the $R^{30}$ radical is selected from the group consisting of hydrogen, unbranched or branched alkyl group having 1 to 6 carbon atoms.

6.7 Process according to one or more of Points 6.1 to 6.6, where $X^9$=hydrogen.

6.8 Process according to one or more of Points 6.1 to 6.7, wherein formaldehyde is used as a gas, as an aqueous solution or as a solid, preferably as an aqueous solution or as a solid, more preferably as an aqueous solution.

6.9 Process according to one or more of Points 6.1 to 6.8, wherein the at least one triacetonamine compound (I) is reacted with formaldehyde under reductive conditions in at least one solvent, where the solvent is selected from the group consisting of aliphatic solvents, aromatic solvents, ethers, halogenated solvents, amides, thio compounds, carboxylic acids, alcohols, water.

6.10 Process according to one or more of Points 6.1 to 6.9, wherein the at least one triacetonamine compound (I) is reacted with formaldehyde under reductive conditions at a temperature in the range from 20° C. to 350° C. and a pressure in the range from 2 bar to 500 bar.

The present invention relates, in a seventh aspect, to a process according to the following Points 7.1 to 7.9:

7.1 Process for preparing an N-methyl-substituted triacetonamine compound,
characterized in that at least one triacetonamine compound (I) is reacted with formaldehyde under reductive conditions,
where the triacetonamine compound (I) has the chemical structure (I-F) with

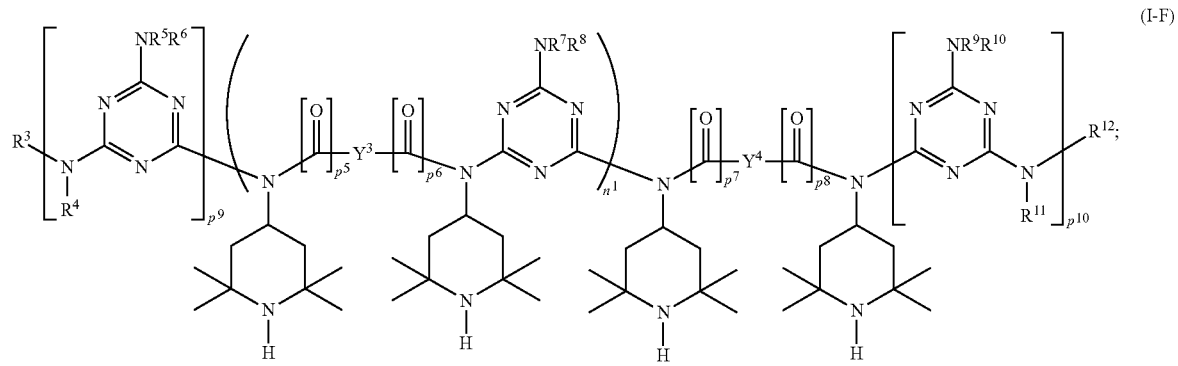

(I-F)

a radical having a chemical structure (ix) with

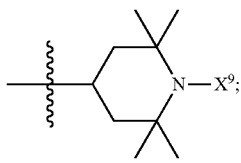

(ix)

where $X^9$ is selected from the group consisting of hydrogen, —OH, —O., unbranched or branched alkyl group having 1 to 10 carbon atoms, unbranched or branched alkoxy group having 1 to 10 carbon atoms.

where $n^1$ is an integer from the range of 1 to 20;
where $p^5$, $p^6$, $p^7$, $p^8$, $p^9$, $p^{10}$ are each independently 0 or 1;
where $Y^3$, $Y^4$ are each independently selected from the group consisting of
unbranched or branched alkylene group having 1 to 30 carbon atoms, divalent saturated hydrocarbyl group having 3 to 30 carbon atoms and having at least one saturated ring composed of 3 to 30 carbon atoms, divalent hydrocarbyl group having 6 to 30 carbon atoms, of which at least 6 carbon atoms are present in an aromatic system and the other carbon atoms, if present, are saturated, a bridging radical having a chemical structure selected from the group consisting of (i), (ii) with (i)

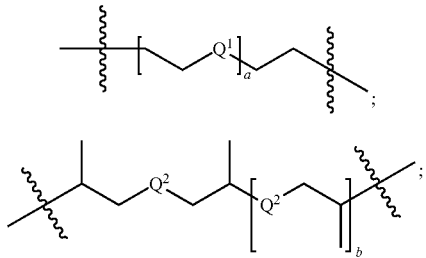

(ii)

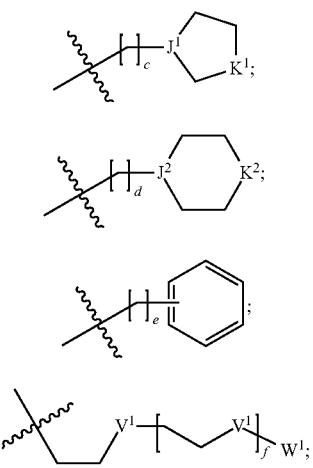

where
Q$^1$, Q$^2$ are each independently selected from the group consisting of —O—, —S—, —NH— and —NR'— with R'=unbranched or branched alkyl group having 1 to 6 carbon atoms,
where a is an integer selected from the range of 1 to 50,
where b is an integer selected from the range of 0 to 50,
and where Y$^3$ may also be a direct bond if at least one of p$^5$ and p$^6$ has the value of 1,
and where Y$^4$ may also be a direct bond if at least one of p$^7$ and p$^8$ has the value of 1,
where the R$^3$, R$^4$, R$^5$, R$^6$, R$^9$, R$^{10}$, R$^{11}$, R$^{12}$ radicals are each independently selected from the group consisting of
hydrogen,
unbranched or branched alkyl group which has 1 to 30 carbon atoms and in which at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$),
unbranched or branched acyl group which has 1 to 30 carbon atoms and in which at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$);
a radical having a chemical structure selected from the group consisting of (iii), (iv), (v), (vi), (vii), (viii), (ix) with (iii)

(iv)

(v)

(vi)

-continued (vii)

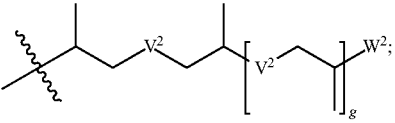

(viii)

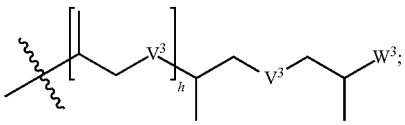

(ix)

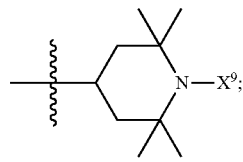

where J$^1$, J$^2$ are each independently selected from the group consisting of CH, N,
where K$^1$, K$^2$ are each independently selected from the group consisting of —O—, —NH—, —N(CH$_3$)—, —N(CH$_2$CH$_3$)—, —S—, —CH$_2$—,
where V$^1$, V$^2$, V$^3$ are each independently selected from the group consisting of —O—, —S—, —NH—, —NR''— with R''=unbranched or branched alkyl group having 1 to 6 carbon atoms,
where W$^1$, W$^2$, W$^3$ are each independently selected from the group consisting of H, methyl, ethyl,
where c, d, e, f, g, h are each independently an integer from the range of 0 to 50,
where X$^9$ is selected from the group consisting of hydrogen, —OH, —O., unbranched or branched alkyl group having 1 to 10 carbon atoms, unbranched or branched alkoxy group having 1 to 10 carbon atoms,
where, in the chemical structures (iii), (iv), (v), (vi), (vii), (viii), (ix), at least one hydrogen radical bonded to a carbon atom may be replaced by a radical selected from the group consisting of
—OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$);
where the R$^7$, R$^8$ radicals are each independently selected from the group consisting of
hydrogen,
unbranched or branched alkyl group which has 1 to 30 carbon atoms and in which at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$),
unbranched or branched acyl group which has 1 to 30 carbon atoms and in which at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$);
and where, when p$^9$=1, —NR$^3$R$^4$ may also be a radical of the chemical structure (x),
and where, when p$^{10}$=1, —NR$^{11}$R$^{12}$ may also be a radical of the chemical structure (x),
and where the —NR$^5$R$^6$, —NR$^7$R$^8$, —NR$^9$R$^{10}$ radicals may each independently also be a radical of the chemical structure (x), where the chemical structure (x) is defined as follows:

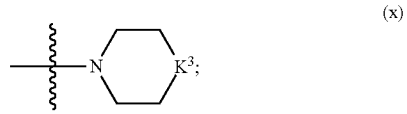

where $K^3$ is selected from the group consisting of —O—, —S—, —NH—, —N(CH$_3$)—, —N(CH$_2$CH$_3$)—, where $K^3$ is preferably —O—, and wherein reductive conditions are established by reacting the at least one triacetonamine compound (I) with formaldehyde in the presence of hydrogen and in the presence of an unsupported catalyst, where the unsupported catalyst includes at least one metal M, where the metal M is selected from the group consisting of Ag, V, Cr, Mo, Mn, Ni, Pd, Pt, Fe, Ru, Os, Co, Rh, Ir, Cu, especially Ag, Fe, Ni, Co, Cu, preferably Ni, Co, more preferably Ni.

7.2 Process according to Point 7.1, where $p^5=p^6=p^7=p^8=0$ and where $p^9$, $p^{10}$ are each independently 0 or 1; preferably, $p^5=p^6=p^7=p^8=0$ and at least one of $p^9$, $p^{10}$ is 1 (where, logically, if only one of $p^9$, $p^{10}=1$, the other of $p^9$, $p^{10}=0$); even more preferably, $p^5=p^6=p^7=p^8=0$ and $p^9=p^{10}=1$.

7.3 Process according to Point 7.1 or 7.2, where $Y^3$, $Y^4$ are each independently selected from the group consisting of
unbranched or branched alkylene group having 1 to 30 carbon atoms,
divalent saturated hydrocarbyl group having 3 to 30 carbon atoms and having at least one saturated ring composed of 3 to 30 carbon atoms.

7.4 Process according to one or more of Points 7.1 to 7.3, where the $R^3$, $R^4$, $R^5$, $R^6$, $R^9$, $R^{10}$, $R^{11}$, $R^{12}$ radicals are each independently selected from the group consisting of
hydrogen,
unbranched or branched alkyl group which has 1 to 30 carbon atoms and in which at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$),
a radical having a chemical structure (ix) with

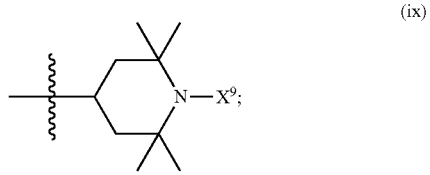

where $X^9$ is selected from the group consisting of hydrogen, —OH, —O., unbranched or branched alkyl group having 1 to 10 carbon atoms, unbranched or branched alkoxy group having 1 to 10 carbon atoms;
where the $R^7$, $R^8$ radicals are each independently selected from the group consisting of
hydrogen,
unbranched or branched alkyl group which has 1 to 30 carbon atoms and in which at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$), and where, when $p^9=1$, —NR$^3$R$^4$ may also be a radical of the chemical structure (x), and where, when $p^{10}=1$, —NR$^{11}$R$^{12}$ may also be a radical of the chemical structure (x), and where the —NR$^5$R$^6$, —NR$^7$R$^8$, —NR$^9$R$^{10}$ radicals may each independently also be a radical of the chemical structure (x), where the chemical structure (x) is defined as follows:

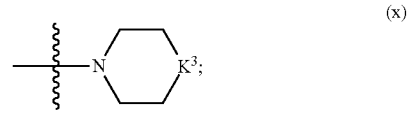

where $K^3$ is selected from the group consisting of —O—, —S—, —NH—, —N(CH$_3$)—, —N(CH$_2$CH$_3$)—, where $K^3$ is preferably —O—.

7.5 Process according to one or more of Points 7.1 to 7.4, where the $R^3$, $R^4$, $R^5$, $R^6$, $R^9$, $R^{10}$, $R^{11}$, $R^{12}$ radicals are each independently selected from the group consisting of
hydrogen,
unbranched or branched alkyl group having 1 to 12 carbon atoms,
a radical having a chemical structure (ix) with

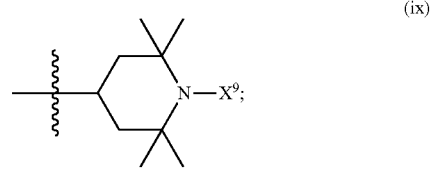

where $X^9$ is selected from the group consisting of hydrogen, —OH, —O., unbranched or branched alkyl group having 1 to 10 carbon atoms, unbranched or branched alkoxy group having 1 to 10 carbon atoms;
where the $R^7$, $R^8$ radicals are each independently selected from the group consisting of
hydrogen,
unbranched or branched alkyl group having 1 to 12 and preferably 1 to 6 carbon atoms,
and where the —NR$^7$R$^8$ radical may also be a radical of the chemical structure (x) with

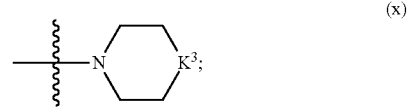

where $K^3$=—O—.

7.6 Process according to one or more of Points 7.1 to 7.5, where $X^9$=hydrogen.

7.7 Process according to one or more of Points 7.1 to 7.6, wherein formaldehyde is used as a gas, as an aqueous solution or as a solid, preferably as an aqueous solution or as a solid, more preferably as an aqueous solution.

7.8 Process according to one or more of Points 7.1 to 7.7, wherein the at least one triacetonamine compound (I) is reacted with formaldehyde under reductive conditions in at least one solvent, where the solvent is selected from the group consisting of aliphatic solvents, aromatic solvents, ethers, halogenated solvents, amides, thio compounds, carboxylic acids, alcohols, water.

7.9 Process according to one or more of Points 7.1 to 7.8, wherein the at least one triacetonamine compound (I) is reacted with formaldehyde under reductive conditions at a temperature in the range from 20° C. to 350° C. and a pressure in the range from 2 bar to 500 bar.

The present invention relates, in an eighth aspect, to a process according to the following Points 8.1 to 8.9:

8.1 Process for preparing an N-methyl-substituted triacetonamine compound, characterized in that at least one triacetonamine compound (I) is reacted with formaldehyde under reductive conditions, where the triacetonamine compound (I) has the chemical structures (I-G) with

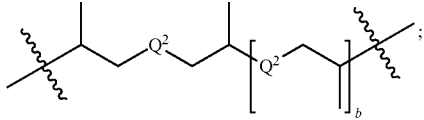
(ii)

where $Q^1$, $Q^2$ are each independently selected from the group consisting of —O—, —S—, —NH— and —NR'— with R'=unbranched or branched alkyl group having 1 to 6 carbon atoms, where a is an integer selected from the range of 1 to 50, where b is an integer selected from the range of 0 to 50,

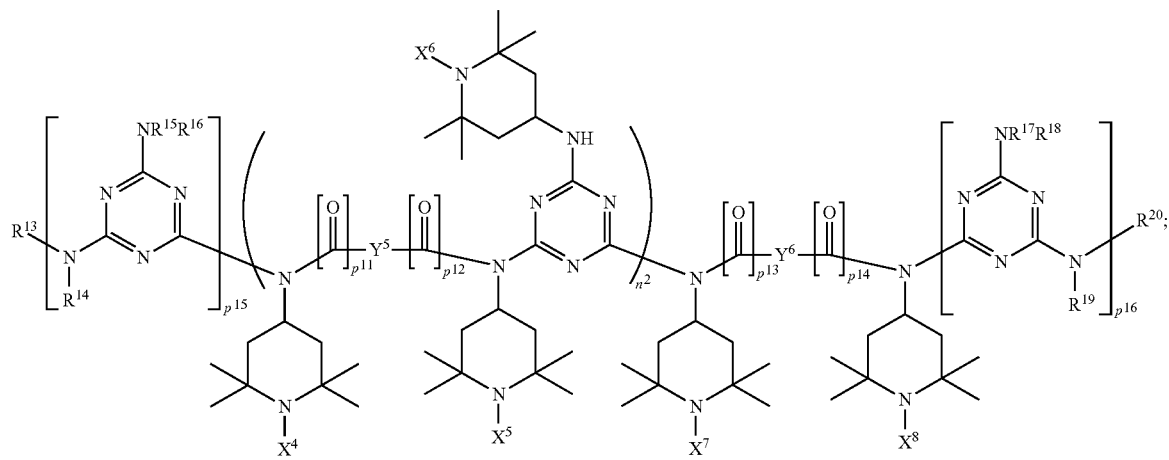
(I-G)

where $n^2$ is an integer from the range of 1 to 20;

where $p^{11}$, $p^{12}$, $p^{13}$, $p^{14}$, $p^{15}$, $p^{16}$ are each independently 0 or 1;

where $X^4$, $X^5$, $X^6$, $X^7$, $X^8$ are each independently selected from the group consisting of hydrogen, OH, —O., unbranched or branched alkyl group having 1 to 10 carbon atoms, unbranched or branched alkoxy group having 1 to 10 carbon atoms;

where $Y^5$, $Y^6$ are each independently selected from the group consisting of unbranched or branched alkylene group having 1 to 30 carbon atoms, divalent saturated hydrocarbyl group having 3 to 30 carbon atoms and having at least one saturated ring composed of 3 to 30 carbon atoms, divalent hydrocarbyl group having 6 to 30 carbon atoms, of which at least 6 carbon atoms are present in an aromatic system and the other carbon atoms, if present, are saturated, a bridging radical having a chemical structure selected from the group consisting of (i), (ii) with and where $Y^5$ may also be a direct bond if at least one of $p^{11}$ and $p^{12}$ has the value of 1, and where $Y^6$ may also be a direct bond if at least one of $p^{13}$ and $p^{14}$ has the value of 1;

where the $R^{13}$, $R^{14}$, $R^{15}$, $R^{16}$, $R^{17}$, $R^{18}$, $R^{19}$, $R^{20}$ radicals are each independently selected from the group consisting of hydrogen, unbranched or branched alkyl group which has 1 to 30 carbon atoms and in which at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$), unbranched or branched acyl group which has 1 to 30 carbon atoms and in which at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$);

a radical having a chemical structure selected from the group consisting of (iii), (iv), (v), (vi), (vii), (viii), (ix) with

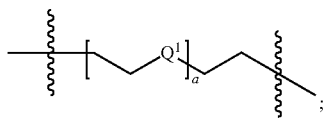
(i)

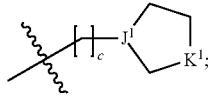
(iii)

-continued

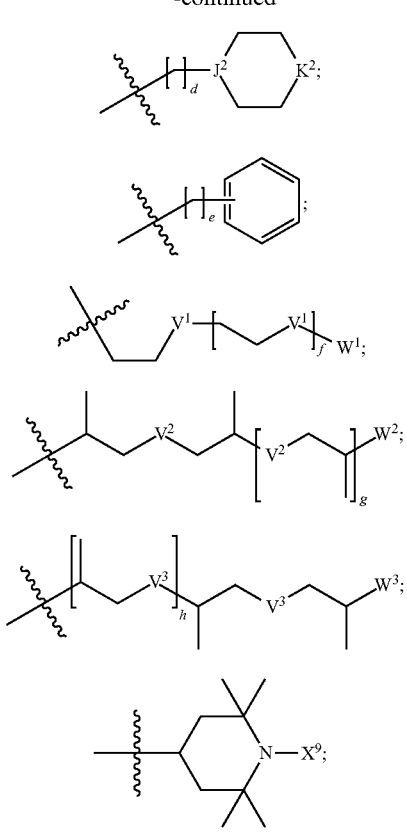

(iv)

(v)

(vi)

(vii)

(viii)

(ix)

where $J^1$, $J^2$ are each independently selected from the group consisting of CH, N,
where $K^1$, $K^2$ are each independently selected from the group consisting of —O—, —NH—, —N(CH$_3$)—, —N(CH$_2$CH$_3$)—, —S—, —CH$_2$—,
where $V^1$, $V^2$, $V^3$ are each independently selected from the group consisting of —O—, —S—, —NH—, —NR''— with R''=unbranched or branched alkyl group having 1 to 6 carbon atoms,
where $W^1$, $W^2$, $W^3$ are each independently selected from the group consisting of H, methyl, ethyl,
where c, d, e, f, g, h are each independently an integer from the range of 0 to 50,
where $X^9$ is selected from the group consisting of hydrogen, —OH, —O., unbranched or branched alkyl group having 1 to 10 carbon atoms, unbranched or branched alkoxy group having 1 to 10 carbon atoms,
where, in the chemical structures (iii), (iv), (v), (vi), (vii), (viii), (ix), at least one hydrogen radical bonded to a carbon atom may be replaced by a radical selected from the group consisting of
—OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$),
and wherein reductive conditions are established by reacting the at least one triacetonamine compound (I) with formaldehyde in the presence of hydrogen and in the presence of an unsupported catalyst, where the unsupported catalyst includes at least one metal M, where the metal M is selected from the group consisting of Ag, V, Cr, Mo, Mn, Ni, Pd, Pt, Fe, Ru, Os, Co, Rh, Ir, Cu, especially Ag, Fe, Ni, Co, Cu, preferably Ni, Co, more preferably Ni.

8.2 Process according to Point 8.1, where $p^{11}=p^{12}=p^{13}=p^{14}=0$ and where $p^{15}$, $p^{16}$ are each independently 0 or 1.

8.3 Process according to Point 8.1 or 8.2, where
$Y^5$, $Y^6$ are each independently selected from the group consisting of
unbranched or branched alkylene group having 1 to 30 carbon atoms,
divalent saturated hydrocarbyl group having 3 to 30 carbon atoms and having at least one saturated ring composed of 3 to 30 carbon atoms.

8.4 Process according to one or more of Points 8.1 to 8.3, where the $R^{13}$, $R^{14}$, $R^{15}$, $R^{16}$, $R^{17}$, $R^{18}$, $R^{19}$, $R^{20}$ radicals are each independently selected from the group consisting of
hydrogen,
unbranched or branched alkyl group which has 1 to 30 carbon atoms and in which at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$),
a radical having a chemical structure (ix) with

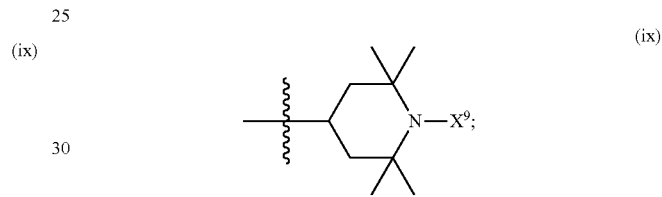

(ix)

where $X^9$ is selected from the group consisting of hydrogen, —OH, —O., unbranched or branched alkyl group having 1 to 10 carbon atoms, unbranched or branched alkoxy group having 1 to 10 carbon atoms.

8.5 Process according to one or more of Points 8.1 to 8.4, where the $R^{13}$, $R^{14}$, $R^{15}$, $R^{16}$, $R^{17}$, $R^{18}$, $R^{19}$, $R^{20}$ radicals are each independently selected from the group consisting of
hydrogen,
unbranched or branched alkyl group having 1 to 12 and preferably 1 to 6 carbon atoms,
a radical having a chemical structure (ix) with

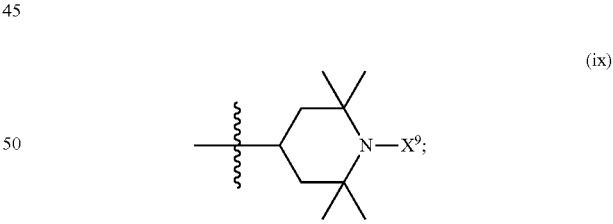

(ix)

where $X^9$ is selected from the group consisting of hydrogen, —OH, —O., unbranched or branched alkyl group having 1 to 10 carbon atoms, unbranched or branched alkoxy group having 1 to 10 carbon atoms.

8.6 Process according to one or more of Points 8.1 to 8.5, where $X^4=X^5=X^6=X^7=X^8=X^9=$hydrogen.

8.7 Process according to one or more of Points 8.1 to 8.6, wherein formaldehyde is used as a gas, as an aqueous solution or as a solid, preferably as an aqueous solution or as a solid, more preferably as an aqueous solution.

8.8 Process according to one or more of Points 8.1 to 8.7, wherein the at least one triacetonamine compound (I) is reacted with formaldehyde under reductive conditions in at least one solvent, where the solvent is selected from the group consisting of aliphatic solvents, aromatic solvents, ethers, halogenated solvents, amides, thio compounds, carboxylic acids, alcohols, water.

8.9 Process according to one or more of Points 8.1 to 8.8, wherein the at least one triacetonamine compound (I) is reacted with formaldehyde under reductive conditions at a temperature in the range from 20° C. to 350° C. and a pressure in the range from 2 bar to 500 bar.

The present invention relates, in a ninth aspect, to a process according to the following Points 9.1 to 9.8:

9.1 Process for preparing an N-methyl-substituted triacetonamine compound, characterized in that at least one triacetonamine compound (I) is reacted with formaldehyde under reductive conditions, where the triacetonamine compound (I) has the chemical structures (I-H) with (I-H)

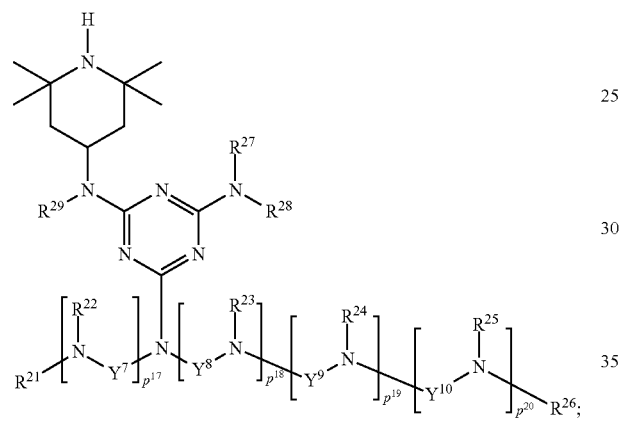

where $p^{17}$, $p^{18}$, $p^{19}$, $p^{20}$ are each independently 0 or 1;
where $Y^7$, $Y^8$, $Y^9$, $Y^{10}$ are each independently selected from the group consisting of
  unbranched or branched alkylene group having 1 to 30 carbon atoms,
  divalent saturated hydrocarbyl group having 3 to 30 carbon atoms and having at least one saturated ring composed of 3 to 30 carbon atoms,
  divalent hydrocarbyl group having 6 to 30 carbon atoms, of which at least 6 carbon atoms are present in an aromatic system and the other carbon atoms, if present, are saturated,
  a bridging radical having a chemical structure selected from the group consisting of (i), (ii) with (i)

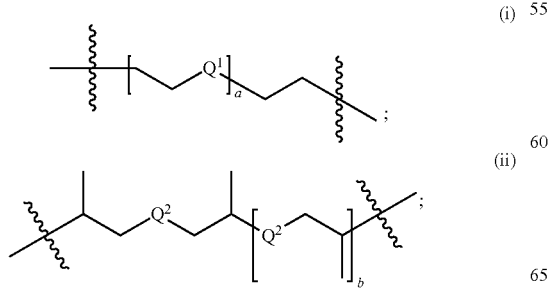

(ii)

where
$Q^1$, $Q^2$ are each independently selected from the group consisting of —O—, —S—, —NH— and —NR'— with R'=unbranched or branched alkyl group having 1 to 6 carbon atoms,
where a is an integer selected from the range of 1 to 50,
where b is an integer selected from the range of 0 to 50,
where the $R^{21}$, $R^{22}$, $R^{23}$, $R^{24}$, $R^{25}$, $R^{26}$ radicals are each independently selected from the group consisting of
hydrogen,
unbranched or branched alkyl group having 1 to 30 carbon atoms,
a group having the chemical structure (xi) with (xi)

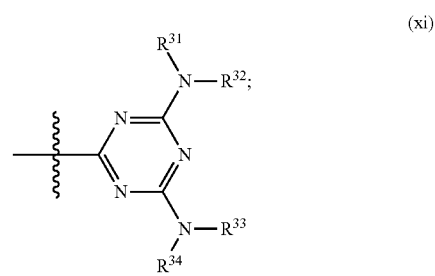

where the $R^{27}$, $R^{28}$, $R^{29}$, $R^{31}$, $R^{32}$, $R^{33}$, $R^{34}$ radicals are each independently selected from the group consisting of
hydrogen,
unbranched or branched alkyl group which has 1 to 30 carbon atoms and in which at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$),
unbranched or branched acyl group which has 1 to 30 carbon atoms and in which at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$);
a radical having a chemical structure selected from the group consisting of (xii), (xiii), (xiv), (xv), (xvi), (xvii), (xviii) with (xii)

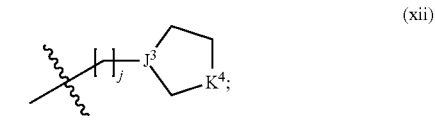

(xiii)

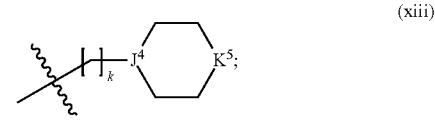

(xiv)

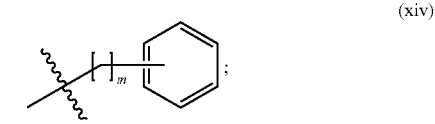

(xv)

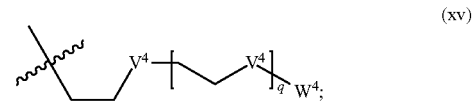

-continued

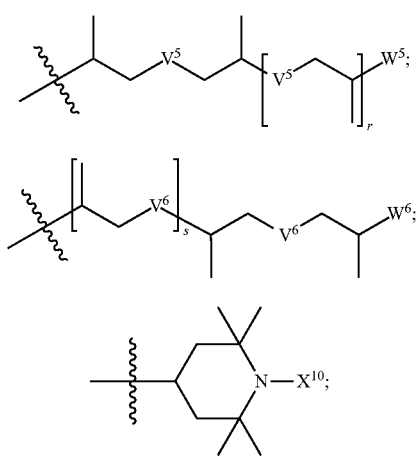

where $J^3$, $J^4$ are each independently selected from the group consisting of CH, N, where $K^4$, $K^5$ are each independently selected from the group consisting of —O—, —NH—, —N(CH$_3$)—, —N(CH$_2$CH$_3$)—, —S—, —CH$_2$—, where $V^4$, $V^5$, $V^6$ are each independently selected from the group consisting of —O—, —S—, —NH—, —NR'''— with R'''=unbranched or branched alkyl group having 1 to 6 carbon atoms, where $W^4$, $W^5$, $W^6$ are each independently selected from the group consisting of H, methyl, ethyl, where j, k, m, q, r, s are each independently an integer from the range of 0 to 50, where $X^{10}$ is selected from the group consisting of hydrogen, —OH, —O., unbranched or branched alkyl group having 1 to 10 carbon atoms, unbranched or branched alkoxy group having 1 to 10 carbon atoms, where, in the chemical structures (xii), (xiii), (xiv), (xv), (xvi), (xvii), (xviii), at least one hydrogen radical bonded to a carbon atom may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$), and with the proviso that $R^{21}$ and $R^{26}$, when $p^{17}=p^{18}=p^{19}=p^{20}=0$, may each independently also be a group of the chemical structure (xix) with

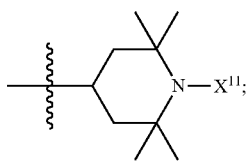

where $X^{11}$ is selected from the group consisting of hydrogen, OH, —O., unbranched or branched alkyl group having 1 to 10 carbon atoms, unbranched or branched alkoxy group having 1 to 10 carbon atoms, and wherein reductive conditions are established by reacting the at least one triacetonamine compound (I) with formaldehyde in the presence of hydrogen and in the presence of an unsupported catalyst, where the unsupported catalyst includes at least one metal M, where the metal M is selected from the group consisting of Ag, V, Cr, Mo, Mn, Ni, Pd, Pt, Fe, Ru, Os, Co, Rh, Ir, Cu, especially Ag, Fe, Ni, Co, Cu, preferably Ni, Co, more preferably Ni.

9.2 Process according to Point 9.1, where $Y^7$, $Y^8$, $Y^9$, $Y^{10}$ are each independently selected from the group consisting of unbranched or branched alkylene group having 1 to 30 carbon atoms, divalent saturated hydrocarbyl group having 3 to 30 carbon atoms and having at least one saturated ring composed of 3 to 30 carbon atoms.

9.3 Process according to one or more of Points 9.1 to 9.2, where the $R^{21}$, $R^{22}$, $R^{23}$, $R^{24}$, $R^{25}$, $R^{26}$ radicals are each independently selected from the group consisting of hydrogen, unbranched or branched alkyl group having 1 to 30 carbon atoms, a group having the chemical structure (xi) with

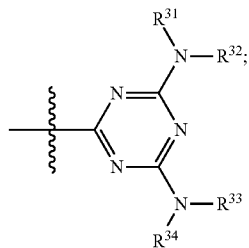

where the $R^{27}$, $R^{28}$, $R^{29}$, $R^{31}$, $R^{32}$, $R^{33}$, $R^{34}$ radicals are each independently selected from the group consisting of hydrogen, unbranched or branched alkyl group which has 1 to 30 carbon atoms and in which at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$), a radical having a chemical structure (xvii) with

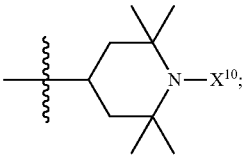

where $X^{10}$ is selected from the group consisting of hydrogen, OH, —O., unbranched or branched alkyl group having 1 to 10 carbon atoms, unbranched or branched alkoxy group having 1 to 10 carbon atoms, and with the proviso that $R^{21}$ and $R^{26}$, when $p^{17}=p^{18}=p^{19}=p^{20}=0$, may each independently also be a group of the chemical structure (xix) with

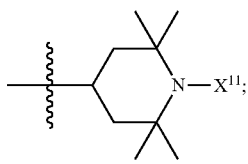

where $X^{11}$ is selected from the group consisting of hydrogen, —OH, —O., unbranched or branched alkyl group having 1 to 10 carbon atoms, unbranched or branched alkoxy group having 1 to 10 carbon atoms.

9.4 Process according to one or more of Points 9.1 to 9.3, where the $R^{21}$, $R^{22}$, $R^{23}$, $R^{24}$, $R^{25}$, $R^{26}$ radicals are each independently selected from the group consisting of
hydrogen,
unbranched or branched alkyl group having 1 to 12 and preferably 1 to 6 carbon atoms,
a group having the chemical structure (xi) with

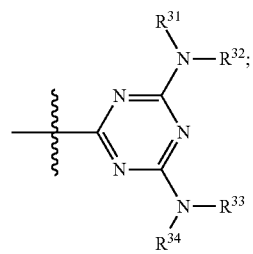

where the $R^{27}$, $R^{28}$, $R^{29}$, $R^{31}$, $R^{32}$, $R^{33}$, $R^{34}$ radicals are each independently selected from the group consisting of
hydrogen,
unbranched or branched alkyl group having 1 to 12 and preferably 1 to 6 carbon atoms,
a radical having a chemical structure (xviii) with

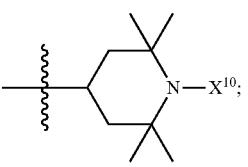

where $X^{10}$ is selected from the group consisting of hydrogen, —OH, —O., unbranched or branched alkyl group having 1 to 10 carbon atoms, unbranched or branched alkoxy group having 1 to 10 carbon atoms,
and with the proviso that $R^{21}$ and $R^{26}$, when $p^{17}=p^{18}=p^{19}=p^{20}=0$, may each independently also be a group of the chemical structure (xix) with

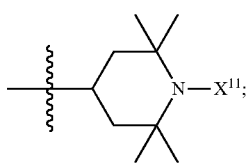

where $X^{11}$ is selected from the group consisting of hydrogen, OH, —O., unbranched or branched alkyl group having 1 to 10 carbon atoms, unbranched or branched alkoxy group having 1 to 10 carbon atoms.

9.5 Process according to one or more of Points 9.1 to 9.4, where
$X^9=X^{10}=X^{11}$=hydrogen.

9.6 Process according to one or more of Points 9.1 to 9.5, wherein formaldehyde is used as a gas, as an aqueous solution or as a solid, preferably as an aqueous solution or as a solid, more preferably as an aqueous solution.

9.7 Process according to one or more of Points 9.1 to 9.6, wherein the at least one triacetonamine compound (I) is reacted with formaldehyde under reductive conditions in at least one solvent, where the solvent is selected from the group consisting of aliphatic solvents, aromatic solvents, ethers, halogenated solvents, amides, thio compounds, carboxylic acids, alcohols, water.

9.8 Process according to one or more of Points 9.1 to 9.7, wherein the at least one triacetonamine compound (I) is reacted with formaldehyde under reductive conditions at a temperature in the range from 20° C. to 350° C. and a pressure in the range from 2 bar to 500 bar.

General Terms

In the context of the invention, an "unbranched or branched alkyl group" is a monovalent saturated hydrocarbyl radical of the general chemical structure (a) with

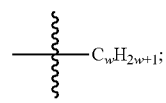

The chain of carbon atoms "—$C_wH_{2w+1}$" may be linear, in which case the group is an unbranched alkyl group. Alternatively, it may have branches, in which case it is a branched alkyl group.

w in the chemical structure (a) is an integer, w in an unbranched or branched alkyl group having 1 to 30 carbon atoms is selected from the range of 1 to 30. w in an unbranched or branched alkyl group having 1 to 29 carbon atoms is selected from the range of 1 to 29. w in an unbranched or branched alkyl group having 1 to 12 carbon atoms is selected from the range of 1 to 12. w in an unbranched or branched alkyl group having 1 to 10 carbon atoms is selected from the range of 1 to 10. w in an unbranched or branched alkyl group having 1 to 8 carbon atoms is selected from the range of 1 to 8. w in an unbranched or branched alkyl group having 1 to 6 carbon atoms is selected from the range of 1 to 6.

In the context of the invention, an "unbranched or branched alkyl group having 1 to 30 carbon atoms" is especially selected from methyl, ethyl, n-propyl, iso-propyl, n-butyl, sec-butyl, iso-butyl, tert-butyl, n-pentyl, 1-methylbutyl, 2-methylbutyl, 3-methylbutyl, 1,1-dimethylpropyl, 1,2-dimethylpropyl, 2,2-dimethylpropyl, 1-ethylpropyl, n-hexyl, 1-methylpentyl, 2-methylpentyl, 3-methylpentyl, 4-methylpentyl, 1, 1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, n-eicosyl, n-heneicosyl, n-docosyl, n-tricosyl, n-tetracosyl, n-pentacosyl, n-hexacosyl, n-heptacosyl, n-octacosyl, n-nonacosyl, n-triacontyl.

In the context of the invention, an "unbranched or branched alkyl group having 1 to 12 carbon atoms" is especially selected from the group consisting of methyl, ethyl, n-propyl, iso-propyl, n-butyl, sec-butyl, iso-butyl, tert-butyl, n-pentyl, 1-methylbutyl, 2-methylbutyl, 3-methylbutyl, 1,1-dimethylpropyl, 1,2-dimethylpropyl, 2,2-dimethylpropyl, 1-ethylpropyl, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl, n-nonyl, n-decyl, n-undecyl, n-dodecyl.

In the context of the invention, an "unbranched or branched alkyl group having 1 to 10 carbon atoms" is especially selected from the group consisting of methyl, ethyl, n-propyl, iso-propyl, n-butyl, sec-butyl, iso-butyl, tert-butyl, n-pentyl, 1-methylbutyl, 2-methylbutyl, 3-methylbutyl, 1,1-dimethylpropyl, 1,2-dimethylpropyl, 2,2-dimethylpropyl, 1-ethylpropyl, n-hexyl, 1-methylpentyl, 2-methylpentyl, 3-methylpentyl, 4-methylpentyl, 1, 1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl, n-nonyl, n-decyl.

In the context of the invention, an "unbranched or branched alkyl group having 1 to 8 carbon atoms" is especially selected from the group consisting of methyl, ethyl, n-propyl, iso-propyl, n-butyl, sec-butyl, iso-butyl, tert-butyl, n-pentyl, 1-methylbutyl, 2-methylbutyl, 3-methylbutyl, 1,1-dimethylpropyl, 1,2-dimethylpropyl, 2,2-dimethylpropyl, I-ethylpropyl, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl.

In the context of the invention, an "unbranched or branched alkyl group having 1 to 6 carbon atoms" is especially selected from the group consisting of methyl, ethyl, n-propyl, iso-propyl, n-butyl, sec-butyl, iso-butyl, tert-butyl, n-pentyl, 1-methylbutyl, 2-methylbutyl, 3-methylbutyl, 1,1-dimethylpropyl, 1,2-dimethylpropyl, 2,2-dimethylpropyl, 1-ethylpropyl, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl.

The term "unbranched or branched alkylene group" in the context of the invention denotes a divalent saturated hydrocarbyl radical which can be described by the general chemical structure (b) with

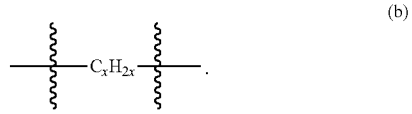

(b)

The chain of carbon atoms "$-C_xH_{2x}-$" may be linear, in which case the group is an unbranched alkylene group. Alternatively, it may have branches, in which case it is a branched alkylene group. x in the chemical structure (b) is an integer.

x in an unbranched or branched alkylene group having 1 to 30 carbon atoms is selected from the range of 1 to 30.

x in an unbranched or branched alkylene group having 1 to 12 carbon atoms is selected from the range of 1 to 12.

x in an unbranched or branched alkylene group having 1 to 6 carbon atoms is selected from the range of 1 to 6.

In the context of the invention, a "divalent saturated hydrocarbyl group having 3 to 30 carbon atoms and having at least one saturated ring composed of 3 to 30 carbon atoms" is especially a chemical structure (c) with

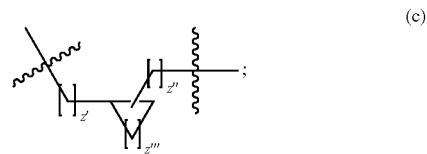

(c)

where $z'$ is an integer from 0 to 27; where $z''$ is an integer from 0 to 27; where $z'''$ is an integer from 1 to 28; and where, at the same time, $z'+z''+z'''\leq 28$.

More particularly, a "divalent saturated hydrocarbyl group having 3 to 30 carbon atoms and having at least one saturated ring composed of 3 to 30 carbon atoms" is a "divalent saturated hydrocarbyl group having 3 to 12 carbon atoms and having at least one saturated ring composed of 3 to 12 carbon atoms", more preferably "divalent saturated hydrocarbyl group having 3 to 6 carbon atoms and having at least one saturated ring composed of 3 to 6 carbon atoms".

A "divalent saturated hydrocarbyl group having 3 to 12 carbon atoms and having at least one saturated ring composed of 3 to 12 carbon atoms" in the context of the invention has a chemical structure (c) where $z'$ is an integer from 0 to 9; where $z''$ is an integer from 0 to 9; where $z'''$ is an integer from 1 to 10; and where, at the same time, $z'+z''+z'''\leq 10$.

Preferably, a "divalent saturated hydrocarbyl group having 3 to 12 carbon atoms and having at least one saturated ring composed of 3 to 12 carbon atoms" is selected from the group consisting of cyclopropylene, cyclobutylene, cyclopentylene, cyclohexylene, cycloheptylene, cyclooctylene, cyclononylene, cyclodecylene, cycloundecylene, cyclododecylene.

A "divalent saturated hydrocarbyl group having 3 to 6 carbon atoms and having at least one saturated ring composed of 3 to 6 carbon atoms" in the context of the invention has a chemical structure (c) where $z'$ is an integer from 0 to 3; where $z''$ is an integer from 0 to 3; where $z'''$ is an integer from 1 to 4; and where, at the same time, $z'+z''+z'''\leq 4$.

Preferably, a "divalent saturated hydrocarbyl group having 3 to 6 carbon atoms and having at least one saturated ring composed of 3 to 6 carbon atoms" is selected from the group consisting of cyclopropylene, cyclobutylene, cyclopentylene, cyclohexylene.

In the context of the invention, a "divalent hydrocarbyl group having 6 to 30 carbon atoms, of which at least 6 carbon atoms are present in an aromatic system and the other carbon atoms, if present, are saturated" is especially a "divalent hydrocarbyl group having 6 to 30 carbon atoms, of which 6, 10 or 14 carbon atoms are present in an aromatic system and the other carbon atoms, if present, are saturated", and is more preferably selected from the group consisting of naphthylene, anthrylene, phenanthrylene and the following chemical structure (d):

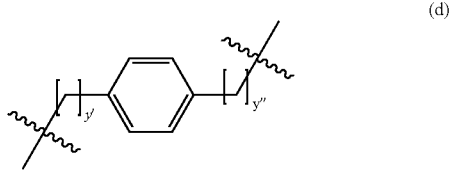
(d)

where y' is an integer from 0 to 24; where y" is an integer from 0 to 24; and where, at the same time, y'+y"≤24.

Even more preferably, it is a "divalent hydrocarbyl group having 6 to 30 carbon atoms, of which 6 or 10 carbon atoms are present in an aromatic system and the other carbon atoms, if present, are saturated", and this group is then most preferably selected from the group consisting of naphthylene and the following chemical structure (d):

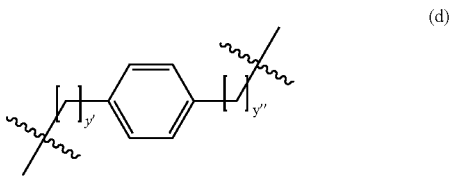
(d)

where y' is an integer from 0 to 24; where y" is an integer from 0 to 24; and where, at the same time, y'+y"≤24.

In the context of the invention, an "unbranched or branched alkoxy group" is an organic radical of the chemical structure

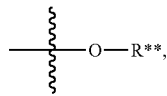

in which R is an unbranched or branched alkyl group. In an "unbranched or branched alkoxy group having 1 to 30 carbon atoms", R is an unbranched or branched alkyl group having 1 to 30 carbon atoms.

In an "unbranched or branched alkoxy group having 1 to 10 carbon atoms", R** is an unbranched or branched alkyl group having 1 to 10 carbon atoms.

In the context of the invention, an "unbranched or branched alkoxy group having 1 to 10 carbon atoms" is especially selected from the group consisting of methoxy, ethoxy, n-propoxy, iso-propoxy, n-butoxy, sec-butoxy, iso-butoxy, tert-butoxy, n-pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, n-hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy, 1-ethyl-2-methylpropoxy, n-heptoxy, n-octoxy, n-nonoxy, n-decoxy.

In the context of the invention, an "unbranched or branched acyl group having 1 to 30 carbon atoms" is an organic radical of the chemical structure

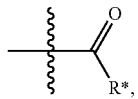

in which R* is an unbranched or branched alkyl radical having 1 to 29 carbon atoms.

More particularly, R* is selected from the group consisting of methyl, ethyl, n-propyl, iso-propyl, n-butyl, sec-butyl, iso-butyl, tert-butyl, n-pentyl, 1-methylbutyl, 2-methylbutyl, 3-methylbutyl, 1,1-dimethylpropyl, 1,2-dimethylpropyl, 2,2-dimethylpropyl, 1-ethylpropyl, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, n-eicosyl, n-heneicosyl, n-docosyl, n-tricosyl, n-tetracosyl, n-pentacosyl, n-hexacosyl, n-heptacosyl, n-octacosyl, n-nonacosyl.

"—O·" in the context of the invention denotes an oxygen-centred free-radical.

In the context of the invention, the wording "at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$)" means that the group in question is in unsubstituted form or, in the group in question, at least one hydrogen radical bonded to a carbon atom, preferably 1 to 5, more preferably 1 to 3 and most preferably 1 to 2 hydrogen radical(s) bonded to the same or different carbon atom(s), is/are replaced by a radical selected from the group consisting of
—OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$).

Process According to the Invention

Formaldehyde is used in the process according to the invention in particular as a gas, as an aqueous solution or as a solid. Preference is given to using formaldehyde in the process according to the invention as an aqueous solution or as a solid (for example as paraformaldehyde).

In the even more preferred embodiment in which formaldehyde is used as an aqueous solution, the concentration of the formaldehyde in the solution is 1.0% to 37% by weight (w/w, "%" relates to the weight of the formaldehyde based on the total weight of aqueous solution). In the case of 37% by weight of formaldehyde, for example, 100 g of aqueous solution contain 37 g of formaldehyde.

The process according to the invention is conducted under reductive conditions. "Reductive conditions" are understood to mean the conditions under which the imine shown in Reaction Scheme <1> is converted to the corresponding amine by addition of hydrogen.

In the process according to the invention, reductive conditions are established by reacting the at least one triacetonamine compound (I) with formaldehyde in the presence of hydrogen and in the presence of an unsupported catalyst, where the unsupported catalyst includes at least one metal M, where the metal M is selected from the group consisting of Ag, V, Cr, Mo, Mn, Ni, Pd, Pt, Fe, Ru, Os, Co, Rh, Ir, Cu; especially selected from the group consisting of Ag, Fe, Cr, Mo, Mn, Ni, Co, Cu, Pd, Pt, Ru, Rh; preferably selected from the group consisting of Ag, Fe, Cr, Ni, Co, Cu, Pd, Pt; more preferably selected from the group consisting of Ag, Fe, Ni, Co, Cu, Pd, Pt; even more preferably selected from the group consisting of Ag, Fe, Ni, Co, Cu; more preferably still selected from the group consisting of Co, Ni, most preferably Ni.

The use of an unsupported catalyst comprising at least one metal M is essential to the process according to the invention.

An "unsupported catalyst" is known to those skilled in the art and is a shaped body fully permeated by the catalytic material. It thus differs from the "supported catalyst" in which the catalytically active component has been applied to a support other than the catalytically active component.

The at least one metal M in the unsupported catalyst is especially in the elemental state or in the form of a compound of the metal M, for example as an oxide or sulphide, but is preferably in the elemental state.

Preferably, the unsupported catalyst comprising at least one metal M is an unsupported catalyst comprising a metal M selected from Ag, Fe, Ni, Co, Cu, especially Ni, Co, preferably Ni.

The unsupported catalyst may be an alloy of the metal M (in which case the metal M is present to an extent of at least >50% by weight in the alloy, based on the total weight of the alloy) and, for example, apart from M, may also comprise at least one metal or semimetal selected from Al, Si, Mg, Zn, Mo, Cr, especially Al.

Even more preferably, the unsupported catalyst comprising at least one metal M is selected from the group consisting of Raney cobalt, Raney copper, Raney silver, Raney iron, Raney nickel, especially selected from Raney nickel, Raney cobalt, most preferably selected from Raney nickel.

In Raney nickel, the proportion of nickel based on the total content of the Raney nickel is especially at least >50% by weight, preferably at least 60% by weight, more preferably at least 70% by weight, even more preferably at least 80% by weight, even more preferably at least 85% by weight, even more preferably still at least 90% by weight, where the Raney nickel especially additionally comprises further metals and or semimetals other than nickel (for example Al, Mo, Si, Mg, Zn, Mo, Cr) in such an amount that the sum total of the weights of nickel and the other metals and semimetals add up to 100% by weight. The Raney nickel may especially be doped with Zn, Mo, Cr, preferably Mo, in order to improve the catalytic properties.

In Raney cobalt, the proportion of cobalt based on the total content of the Raney cobalt is especially at least >50% by weight, preferably at least 60% by weight, more preferably at least 70% by weight, even more preferably at least 80% by weight, even more preferably at least 85% by weight, even more preferably still at least 90% by weight, where the Raney cobalt especially additionally comprises further metals and or semimetals other than cobalt (for example Al, Mo, Si, Mg, Zn, Mo, Cr) in such an amount that the sum total of the weights of cobalt and the other metals and semimetals add up to 100% by weight. The Raney cobalt may especially be doped with Zn, Mo, Cr, preferably Mo, in order to improve the catalytic properties.

In Raney copper, the proportion of copper based on the total content of the Raney copper is especially at least >50% by weight, preferably at least 60% by weight, more prefer-
ably at least 70% by weight, even more preferably at least 80% by weight, even more preferably at least 85% by weight, even more preferably still at least 90% by weight, where the Raney copper especially additionally comprises further metals and or semimetals other than copper (for example Al, Mo, Si, Mg, Zn, Mo, Cr) in such an amount that the sum total of the weights of copper and the other metals and semimetals add up to 100% by weight. The Raney copper may especially be doped with Zn, Mo, Cr, preferably Mo, in order to improve the catalytic properties.

In Raney silver, the proportion of silver based on the total content of the Raney silver is especially at least >50% by weight, preferably at least 60% by weight, more preferably at least 70% by weight, even more preferably at least 80% by weight, even more preferably at least 85% by weight, even more preferably still at least 90% by weight, where the Raney silver especially additionally comprises further metals and or semimetals other than silver (for example Al, Mo, Si, Mg, Zn, Mo, Cr) in such an amount that the sum total of the weights of silver and the other metals and semimetals add up to 100% by weight. The Raney silver may especially be doped with Zn, Mo, Cr, preferably Mo, in order to improve the catalytic properties.

In Raney iron, the proportion of iron based on the total content of the Raney iron is especially at least >50% by weight, preferably at least 60% by weight, more preferably at least 70% by weight, even more preferably at least 80% by weight, even more preferably at least 85% by weight, even more preferably still at least 90% by weight, where the Raney iron especially additionally comprises further metals and or semimetals other than iron (for example Al, Mo, Si, Mg, Zn, Mo, Cr) in such an amount that the sum total of the weights of iron and the other metals and semimetals add up to 100% by weight. The Raney iron may especially be doped with Zn, Mo, Cr, preferably Mo, in order to improve the catalytic properties.

The preparation of the unsupported catalysts according to the invention is known to those skilled in the art. The preparation of Raney nickel is described, for example, in U.S. Pat. No. 1,629,190, DE 20 2010 007837 U1. For this purpose, Ni is alloyed with Al, Si, Mg or Zn (especially with Al, preferably in a ratio of 1:1), and, after mechanical comminution, the catalytically inactive metal (Al) is at least partly leached out of the alloy with alkalis (especially NaOH).

Raney copper, Raney cobalt, Raney silver or Raney iron are also prepared in a corresponding manner (described, for example, in DE 20 2010 007837 U1).

Without such an unsupported catalyst, only unwanted products would be obtained. C. Harries describes, for example, on page 220 to 222 of his article "Untersuchungen über die cyclischen Acetonbasen" [Studies of the Cyclic Acetone Bases] in Justus Liebigs Annalen der Chemie, volume 417, 1918, pages 107 to 191, a reaction of 4-amino-2,2,6,6-tetramethylaminopiperidine with acetic anhydride without unsupported catalyst (or supported catalyst), which leads to high yields of the corresponding amide compound which is unwanted here.

The process according to the invention can be conducted without solvent or else in at least one solvent, preferably in at least one solvent. Suitable solvents are all solvents in which the reactants have good solubility and which also do not have any disruptive influence on the process according to the invention. More particularly, the solvent is selected from the group consisting of aliphatic solvents, aromatic solvents, ethers, halogenated solvents, amides, thio compounds, carboxylic acids, alcohols, water; preferably, the solvent is selected from the group consisting of aliphatic solvents, aromatic solvents, ethers, alcohols, water; more preferably, the solvent is selected from the group consisting of aliphatic solvents, aromatic solvents, ethers, alcohols, water; even more preferably, the solvent is selected from the group consisting of aliphatic solvents, aromatic solvents, alcohols, water. The solvent is more preferably selected from aromatic solvents (especially toluene), alcohols (especially methanol).

Aliphatic solvents are especially selected from the group consisting of pentane, hexane, heptane, octane, decane, cyclopentane, cyclohexane, methylcyclohexane, petroleum ether.

Aromatic solvents are especially selected from the group consisting of benzene, toluene, xylene, ethylbenzene, cumene, bromobenzene, chlorobenzene, dichlorobenzene, furan, preferably toluene.

Ethers are especially selected from the group consisting of diethyl ether, dipropyl ether, dibutyl ether, methyl tert-butyl ether, ethylene glycol monomethyl ether, ethylene glycol monoethyl ether, ethylene glycol dimethyl ether, ethylene glycol diethyl ether, diethylene glycol monomethyl ether, diethylene glycol monoethyl ether, diethylene glycol dimethyl ether, diethylene glycol diethyl ether, triethylene glycol monomethyl ether, triethylene glycol monoethyl ether, triethylene glycol dimethyl ether, triethylene glycol diethyl ether, polyethylene glycol monomethyl ether, polyethylene glycol monoethyl ether, polyethylene glycol dimethyl ether, polyethylene glycol diethyl ether, 1,4-dioxane, 1,3-dioxane, tetrahydrofuran.

Halogenated solvents are especially selected from the group consisting of dichloromethane, chloroform, tetrachloromethane.

Amides are especially selected from the group consisting of dimethylformamide, dimethylacetamide.

Thio compounds are especially selected from the group consisting of dimethyl sulphoxide, sulpholane.

Carboxylic acids are especially selected from the group consisting of formic acid, acetic acid, propionic acid, butanoic acid, pentanoic acid.

Alcohols are especially selected from the group consisting of methanol, ethanol, propanol, iso-propanol, propane-1,2-diol, propane-1,3-diol, glycerol, butanol, sec-butanol, iso-butanol, tert-butanol, butane-1,2-diol, butane-1,3-diol, butane-1,4-diol, pentan-1-ol, pentan-2-ol, pentan-3-ol, tert-amyl alcohol, pentane-1,2-diol, pentane-1,3-diol, pentane-1,4-diol, pentane-1,5-diol, cyclopentanol, hexanol, cyclohexanol, heptanol, octanol, nonanol, decanol, ethylene glycol, diethylene glycol, triethylene glycol, polyethylene glycol, benzyl alcohol, phenol; preferably selected from methanol, ethanol, n-propanol, isopropanol; preferably methanol.

The process according to the invention can be conducted continuously or non-continuously, i.e. batchwise.

The reaction time depends on the progress of the process and on the desired conversion—the aim is typically a maximum possible conversion and the process according to the invention is continued until no further conversion of reactant can be observed.

The temperature in the process according to the invention is not restricted and is preferably in the range from 20° C. to 350° C., more preferably in the range from 50° C. to 300° C., even more preferably in the range from 50° C. to 250° C., most preferably in the range from 70° C. to 200° C., even more preferably 80° C. to 140° C.

The pressure in the process according to the invention is not restricted and is preferably in the range from 2 bar to 500 bar, more preferably in the range from 5 bar to 350 bar, even more preferably in the range from 15 bar to 300 bar, even more preferably 20 to 42 bar.

The above temperature ranges and pressure ranges may of course also be present in combination. Thus, the process can preferably be conducted at a temperature in the range from 20° C. to 350° C., [more preferably in the range from 50° C. to 300° C., even more preferably in the range from 50° C. to 250° C., most preferably in the range from 70° C. to 200° C., even more preferably at 80° C.-140° C.] and a pressure in the range from 2 bar to 500 bar [preferably in the range from 2 bar to 500 bar, more preferably in the range from 5 bar to 350 bar, even more preferably in the range from 15 bar to 300 bar, even more preferably 20 to 42 bar].

This process solves the problems addressed by the invention. It is particularly advantageous that the only by-product that arises in the reaction is water. In addition, the small excess of formaldehyde can either be converted to methanol by hydrogenation or removed by distillation and optionally recycled.

The workup of the crude product is therefore very simple: the catalyst is removed by filtration (it would also be conceivable in technical terms to use a fixed bed catalyst, such that this step would not be needed either), then the crude product is purified by distillation. The distillation affords only methanol (which can be recycled), water, the product and possibly formaldehyde (which can likewise be recycled).

By contrast with the prior art processes, there is thus no need for any separation from the salts formed (which is generally effected by extraction with an additional solvent); in addition, the salts mentioned (or the aqueous solution thereof) are not obtained as a waste stream.

It is additionally advantageous in the process according to the invention that, in addition to the introduction of the methyl group on the piperidine nitrogen ($N^1$), it is also possible to simultaneously methylate other amino groups as well. For example, $N^4$-alkyl-4-amino-2,2,6,6-tetramethylpiperidines can be converted selectively to the $N^1,N^4$-dimethyl-$N^4$-alkyl-4-amino-2,2,6,6-tetramethylpiperidines. In this case, two or more methyl groups are thus introduced simultaneously.

A further advantage is that the presence of tertiary amino groups is also tolerated, without conversion thereof to the quaternary ammonium salts.

The examples which follow are intended to illustrate the invention in detail, without any intention that the invention be restricted to these embodiments.

Having generally described this invention, a further understanding can be obtained by reference to certain specific examples which are provided herein for purposes of illustration only, and are not intended to be limiting unless otherwise specified.

EXAMPLES

37% by weight formalin solution is available from Sigma Aldrich.

n-Butyltriacetonediamine is available from Evonik Industries AG.

Raney nickel and the further unsupported catalysts Ru, Pt, Rh, Pd, Ir and Co are available from Sigma-Aldrich or from Strem.

Inventive Examples I1-I7

A 100 ml pressure autoclave was charged with 53 g of n-butyltriacetonediamine (0.25 mol), 25 ml of toluene and 0.5 mmol of Raney nickel (I1), Ru (I2), Pt (I3), Rh (I4), Pd (I5), Ir (I6) or Co (I7). Thereafter, an aqueous solution comprising 0.25 mol of formaldehyde (37% by weight of formaldehyde, where the percentage was based on the total weight of the solution, i.e. 100 g of solution contain 37 g of formaldehyde) was added, and the reactor was closed.

Hydrogen was injected while stirring (10 bar H$_2$) and the internal autoclave temperature was increased from 60° C. to 90° C. within 1 hour, then maintained at 90° C. for 3 hours. This was followed by conversion at 120° C. for another 1 hour.

The reactor was then cooled down and decompressed. The crude product was discharged and filtered, and then the solvent was first removed (80-120° C., 400 mbar). The residue was subsequently purified by means of a vacuum distillation using a 0.5 m column having random packing.

Then the yield of product and, if appropriate, the yield of the by-product(s) in the crude product obtained was determined by gas chromatography (=GC, for example with an Agilent 5890 or 7890, FID detector).

The results were as follows:

| Experiment | Yield of N$^4$-monomethyl-butyl-TAD (in %) | Yield of N$^1$,N$^4$-dimethyl-butyl-TAD (in %) |
| --- | --- | --- |
| I1 | 87 | 8 |
| I2 | 82 | 11 |
| I3 | 84 | 10 |
| I4 | 88 | 6 |
| I5 | 85 | 13 |
| I6 | 79 | 4 |
| I7 | 62 | 9 |

The results show that, surprisingly, selective methylation at the N$^4$ nitrogen atom was possible by the novel process with high yield.

N$^1$ in the case of n-butyltriacetonediamine refers to the nitrogen atom within the 2,2,6,6-tetramethylpiperidine ring.

N$^4$ in the case of n-butyltriacetonediamine refers to the nitrogen atom outside the 2,2,6,6-tetramethylpiperidine ring.

Also surprising was the particularly good selectivity in the case of Rh (I4) and Ni (I1).

German patent application 102016212379.3 filed Jul. 7, 2016, is incorporated herein by reference.

Numerous modifications and variations on the present invention are possible in light of the above teachings. It is therefore to be understood that within the scope of the appended claims, the invention may be practiced otherwise than as specifically described herein.

The invention claimed is:

1. A process for preparing an N-methyl-substituted triacetonamine compound, comprising:
reacting at least one triacetonamine compound (I) with formaldehyde under reductive conditions,
wherein the triacetonamine compound (I) is selected from the group consisting of the chemical structures (I-D) and (I-E) with

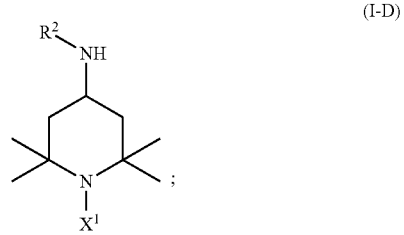

(I-D)

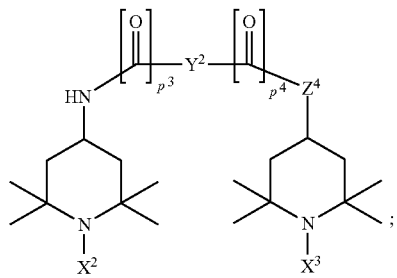

(I-E)

wherein p$^3$, p$^4$ are each independently 0 or 1;
wherein X$^1$, X$^2$, X$^3$ are each hydrogen;
wherein Y$^2$ is selected from the group consisting of
  unbranched or branched alkylene group having 1 to 30 carbon atoms, and
  divalent saturated hydrocarbyl group having 3 to 30 carbon atoms and having at least one saturated ring composed of 3 to 30 carbon atoms,
and wherein Y$^2$ may also be a direct bond if at least one of p$^3$ and p$^4$ has the value of 1;
wherein Z$^4$ is —NR$^{30}$—, and the R$^{30}$ radical is selected from the group consisting of hydrogen and unbranched or branched alkyl group which has 1 to 30 carbon atoms;
wherein the R$^2$ radical is selected from the group consisting of
  hydrogen, and
  unbranched or branched alkyl group which has 1 to 30 carbon atoms and in which at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, and —N(CH$_3$)(CH$_2$CH$_3$);
and wherein reductive conditions are established by reacting the at least one triacetonamine compound (I) with formaldehyde in the presence of hydrogen and in the presence of an unsupported catalyst, wherein the unsupported catalyst is at least one selected from the group consisting of Pd, Pt, Ru, Co, Rh, Ir, and Raney nickel.

2. The process according to claim 1, wherein p$^3$ =p$^4$ =0.

3. The process according to claim 1, wherein the triacetonamine compound (I) is the chemical structure (I-D).

4. The process according to claim 1, wherein the triacetonamine compound (I) is the chemical structure (I-D), wherein the R$^2$ radical is selected from the group consisting of
hydrogen, and
unbranched or branched alkyl group having 1 to 12 carbon atoms.

5. The process according to claim 1, wherein formaldehyde is used as a gas, as an aqueous solution or as a solid.

6. The process according to claim 1, wherein the at least one triacetonamine compound (I) is reacted with formaldehyde under reductive conditions in at least one solvent, wherein the solvent is selected from the group consisting of aliphatic solvents, aromatic solvents, ethers, halogenated solvents, amides, thio compounds, carboxylic acids, alcohols, and water.

7. The process according to claim 1, wherein the at least one triacetonamine compound (I) is reacted with formaldehyde under reductive conditions at a temperature in the range from 20° C. to 350° C. and a pressure in the range from 2 bar to 500 bar.

8. The process according to claim 1, wherein formaldehyde is used as an aqueous solution which has a concentration of formaldehyde of 1.0 to 37% by weight.

9. The process according to claim 1, wherein the at least one triacetonamine compound (I) is reacted with formaldehyde under reductive conditions at a temperature in the range from 50° C. to 250° C. and a pressure in the range from 5 bar to 350 bar.

10. The process according to claim 1, wherein the at least one triacetonamine compound (I) is reacted with formaldehyde under reductive conditions at a temperature in the range from 80° C. to 140° C. and a pressure in the range from 20 bar to 42 bar.

* * * * *